United States Patent
Beith

(10) Patent No.: US 9,301,837 B2
(45) Date of Patent: Apr. 5, 2016

(54) REPLACEMENT HEART VALVES AND THEIR METHODS OF USE AND MANUFACTURE

(71) Applicant: FOLDAX, INC., Salt Lake City, UT (US)

(72) Inventor: Jason G. Beith, Santa Ana, CA (US)

(73) Assignee: FOLDAX, INC., Salt Lake City, UT (US)

( * ) Notice: Subject to any disclaimer, the term of this patent is extended or adjusted under 35 U.S.C. 154(b) by 0 days.

(21) Appl. No.: 14/644,936

(22) Filed: Mar. 11, 2015

(65) Prior Publication Data

US 2015/0320555 A1 Nov. 12, 2015

Related U.S. Application Data

(62) Division of application No. 14/611,071, filed on Jan. 30, 2015.

(60) Provisional application No. 61/991,354, filed on May 9, 2014.

(51) Int. Cl.
*A61F 2/24* (2006.01)
*A61F 2/06* (2013.01)

(52) U.S. Cl.
CPC .............. *A61F 2/2418* (2013.01); *A61F 2/2409* (2013.01); *A61F 2220/0075* (2013.01); *A61F 2230/0069* (2013.01)

(58) Field of Classification Search
CPC ....... A61F 2/2412; A61F 2/2415; A61F 2/24; A61F 2/2418; A61F 2250/0036; A61F 2002/24; A61F 2/2475

USPC .............. 623/1.24, 1.26, 2.14, 2.15, 2.16, 18, 623/2.19

See application file for complete search history.

(56) References Cited

U.S. PATENT DOCUMENTS

| | | | |
|---|---|---|---|
| 3,983,581 A * | 10/1976 | Angell et al. ................ | 623/2.15 |
| 4,222,126 A | 9/1980 | Boretos et al. | |
| 4,265,694 A | 5/1981 | Boretos et al. | |
| 4,291,420 A * | 9/1981 | Reul ..................... | A61F 2/2412 |
| | | | 137/846 |

(Continued)

FOREIGN PATENT DOCUMENTS

| | | |
|---|---|---|
| EP | 2030750 A1 | 3/2009 |
| WO | WO 2013/160651 A1 | 10/2013 |
| WO | PCT/US2015/013980 | 5/2015 |

OTHER PUBLICATIONS

Pibarot, P., et al., "Prosthetic Heart Valves: Selection of the Optimal Prosthesis and Long-Term Management", Circulation, 2009, vol. 119, pp. 1034-1048.

(Continued)

*Primary Examiner* — Alvin Stewart
(74) *Attorney, Agent, or Firm* — One LLP

(57) ABSTRACT

A prosthetic valve has a support structure that meets with a plurality of leaflets capable of transitioning between open and closed states. The support structure can include a base frame with a polymer coating and the leaflets can be artificial. The interface between the support structure and each leaflet can be at least partially convex when viewed from an exterior of the support structure along a normal to a plane formed by a central axis of the support structure and a central axis of the leaflet.

18 Claims, 23 Drawing Sheets
(8 of 23 Drawing Sheet(s) Filed in Color)

(56) References Cited

U.S. PATENT DOCUMENTS

| | | | |
|---|---|---|---|
| 4,364,127 A * | 12/1982 | Pierce et al. | 623/2.19 |
| 4,473,423 A | 9/1984 | Kolff | |
| 4,490,859 A * | 1/1985 | Black | A61F 2/2412 |
| | | | 623/2.16 |
| 4,506,394 A * | 3/1985 | Bedard | A61F 2/2412 |
| | | | 623/2.38 |
| 4,556,996 A | 12/1985 | Wallace | |
| 4,626,255 A * | 12/1986 | Reichart et al. | 623/2.13 |
| 4,759,759 A * | 7/1988 | Walker | A61F 2/2412 |
| | | | 623/2.16 |
| 4,778,461 A * | 10/1988 | Pietsch | A61F 2/2412 |
| | | | 623/2.13 |
| 4,888,009 A * | 12/1989 | Lederman et al. | 623/2.19 |
| 5,147,391 A * | 9/1992 | Lane | 623/2.18 |
| 5,258,023 A * | 11/1993 | Reger | A61F 2/2409 |
| | | | 623/2.18 |
| 5,376,113 A | 12/1994 | Jansen et al. | |
| 5,449,385 A * | 9/1995 | Religa et al. | 623/2.19 |
| 5,489,297 A * | 2/1996 | Duran | 623/2.13 |
| 5,489,298 A * | 2/1996 | Love et al. | 623/2.14 |
| 5,500,016 A * | 3/1996 | Fisher | A61F 2/2412 |
| | | | 623/2.19 |
| 5,549,665 A * | 8/1996 | Vesely | A61F 2/2409 |
| | | | 623/2.14 |
| 5,653,749 A | 8/1997 | Love et al. | |
| 5,861,028 A * | 1/1999 | Angell | 623/2.11 |
| 5,928,281 A * | 7/1999 | Huynh et al. | 623/2.14 |
| 6,117,169 A * | 9/2000 | Moe | A61F 2/2412 |
| | | | 623/2.1 |
| 6,171,335 B1 * | 1/2001 | Wheatley et al. | 623/2.17 |
| 6,174,331 B1 * | 1/2001 | Moe | A61F 2/2412 |
| | | | 623/2.12 |
| 6,283,994 B1 | 9/2001 | Moe et al. | |
| 6,283,995 B1 * | 9/2001 | Moe | A61F 2/2412 |
| | | | 623/2.12 |
| 6,287,334 B1 * | 9/2001 | Moll et al. | 623/1.24 |
| 6,334,873 B1 * | 1/2002 | Lane et al. | 623/2.14 |
| 6,454,798 B1 | 9/2002 | Moe | |
| 6,461,382 B1 * | 10/2002 | Cao | 623/2.19 |
| 6,475,239 B1 * | 11/2002 | Campbell | A61F 2/2412 |
| | | | 264/299 |
| 6,478,819 B2 | 11/2002 | Moe | |
| 6,562,069 B2 * | 5/2003 | Cai | A61F 2/2412 |
| | | | 623/2.12 |
| 6,596,024 B2 | 7/2003 | Chinn | |
| 6,613,086 B1 | 9/2003 | Moe et al. | |
| 6,666,885 B2 * | 12/2003 | Moe | A61F 2/2412 |
| | | | 623/2.12 |
| 6,755,857 B2 * | 6/2004 | Peterson | A61F 2/2409 |
| | | | 623/2.17 |
| 6,780,200 B2 | 8/2004 | Jansen | |
| 6,953,332 B1 * | 10/2005 | Kurk | A61F 2/2415 |
| | | | 249/52 |
| 6,984,700 B2 | 1/2006 | Benz et al. | |
| 7,247,167 B2 * | 7/2007 | Gabbay | 623/2.14 |
| 7,262,260 B2 | 8/2007 | Yilgor et al. | |
| 7,365,134 B2 | 4/2008 | Benz et al. | |
| 7,473,275 B2 * | 1/2009 | Marquez | 623/2.38 |
| 7,563,280 B2 * | 7/2009 | Anderson et al. | 623/2.13 |
| 7,682,389 B2 * | 3/2010 | Beith | 623/2.17 |
| 7,776,084 B2 * | 8/2010 | Johnson | 623/2.19 |
| 7,803,186 B1 * | 9/2010 | Li et al. | 623/2.19 |
| 7,833,565 B2 | 11/2010 | O'Connor et al. | |
| 7,871,435 B2 * | 1/2011 | Carpentier et al. | 623/2.15 |
| 7,959,674 B2 * | 6/2011 | Shu et al. | 623/2.4 |
| 7,988,900 B2 | 8/2011 | Beith | |
| 8,216,631 B2 | 7/2012 | O'Connor et al. | |
| 8,845,720 B2 * | 9/2014 | Conklin | 623/2.14 |
| 2001/0021872 A1 * | 9/2001 | Bailey et al. | 623/1.24 |
| 2002/0062150 A1 | 5/2002 | Campbell et al. | 623/2.18 |
| 2002/0198594 A1 * | 12/2002 | Schreck | 623/2.11 |
| 2005/0096736 A1 * | 5/2005 | Osse et al. | 623/1.26 |
| 2005/0113910 A1 * | 5/2005 | Paniagua et al. | 623/2.14 |
| 2005/0149181 A1 * | 7/2005 | Eberhardt | 623/2.14 |
| 2006/0184239 A1 * | 8/2006 | Andrieu et al. | 623/2.14 |
| 2007/0255400 A1 * | 11/2007 | Parravicini et al. | 623/2.41 |
| 2008/0154358 A1 * | 6/2008 | Tansley et al. | 623/2.14 |
| 2009/0132035 A1 * | 5/2009 | Roth et al. | 623/2.14 |
| 2010/0161045 A1 * | 6/2010 | Righini | 623/2.18 |
| 2011/0282440 A1 * | 11/2011 | Cao et al. | 623/2.18 |
| 2012/0035719 A1 * | 2/2012 | Forster et al. | 623/2.14 |
| 2012/0232646 A1 * | 9/2012 | Agathos | 623/2.19 |
| 2013/0096674 A1 * | 4/2013 | Iobbi | 623/2.19 |
| 2013/0184813 A1 * | 7/2013 | Quadri et al. | 623/2.18 |
| 2013/0268066 A1 * | 10/2013 | Rowe | 623/2.11 |
| 2013/0325116 A1 | 12/2013 | Sundler et al. | |
| 2014/0005773 A1 | 1/2014 | Wheatley | |
| 2014/0114407 A1 * | 4/2014 | Rajamannan | 623/2.18 |
| 2014/0180402 A1 * | 6/2014 | Bruchman et al. | 623/2.18 |
| 2014/0214158 A1 * | 7/2014 | Board et al. | 623/2.14 |

OTHER PUBLICATIONS

Webb, J. G., et al., "Trancatheter Aortic Valve Replacement for Bioprosthetic Aortic Valve Failure: The Valve-in-Valve Procedure", Circulation, 2013, vol. 127, pp. 2542-2550.

Yilgör, E., et al., "Silicone containing copolymers: Synthesis, properties and applications", Progress in Polymer Science, 2014, vol. 39, No. 6, pp. 1165-1195.

* cited by examiner

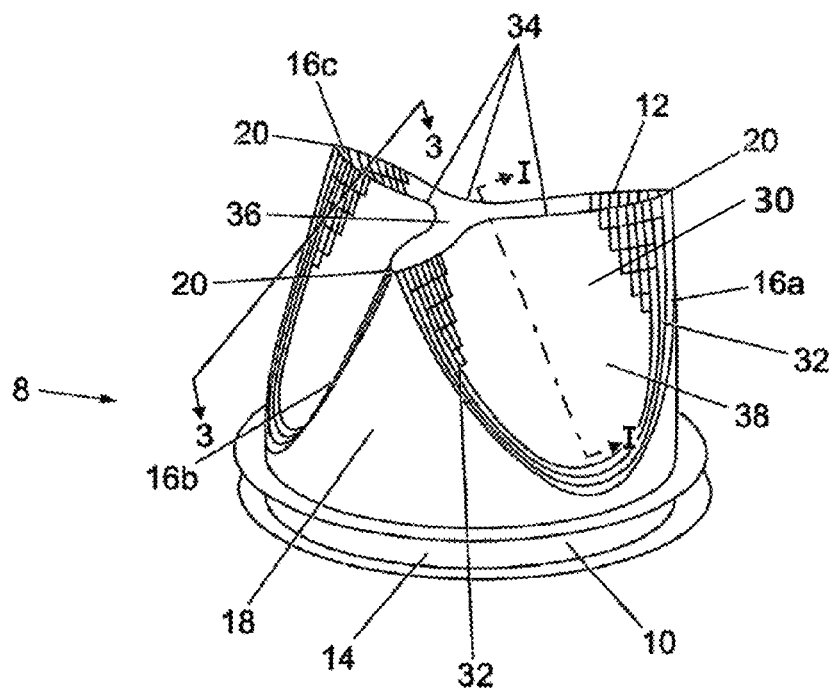
FIG. 1A
(Prior Art)
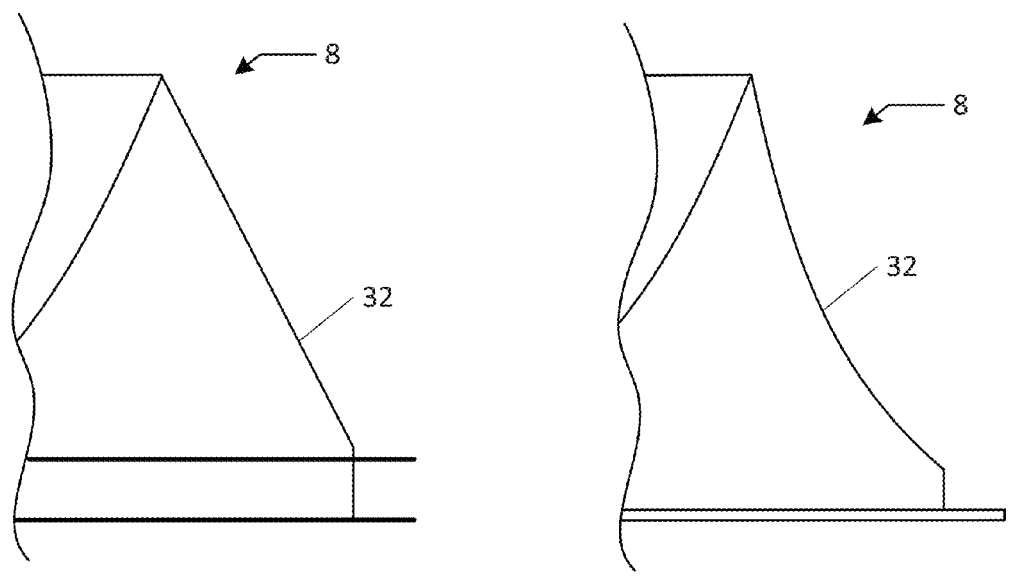
FIG. 1B
(Prior Art)
FIG. 1C
(Prior Art)

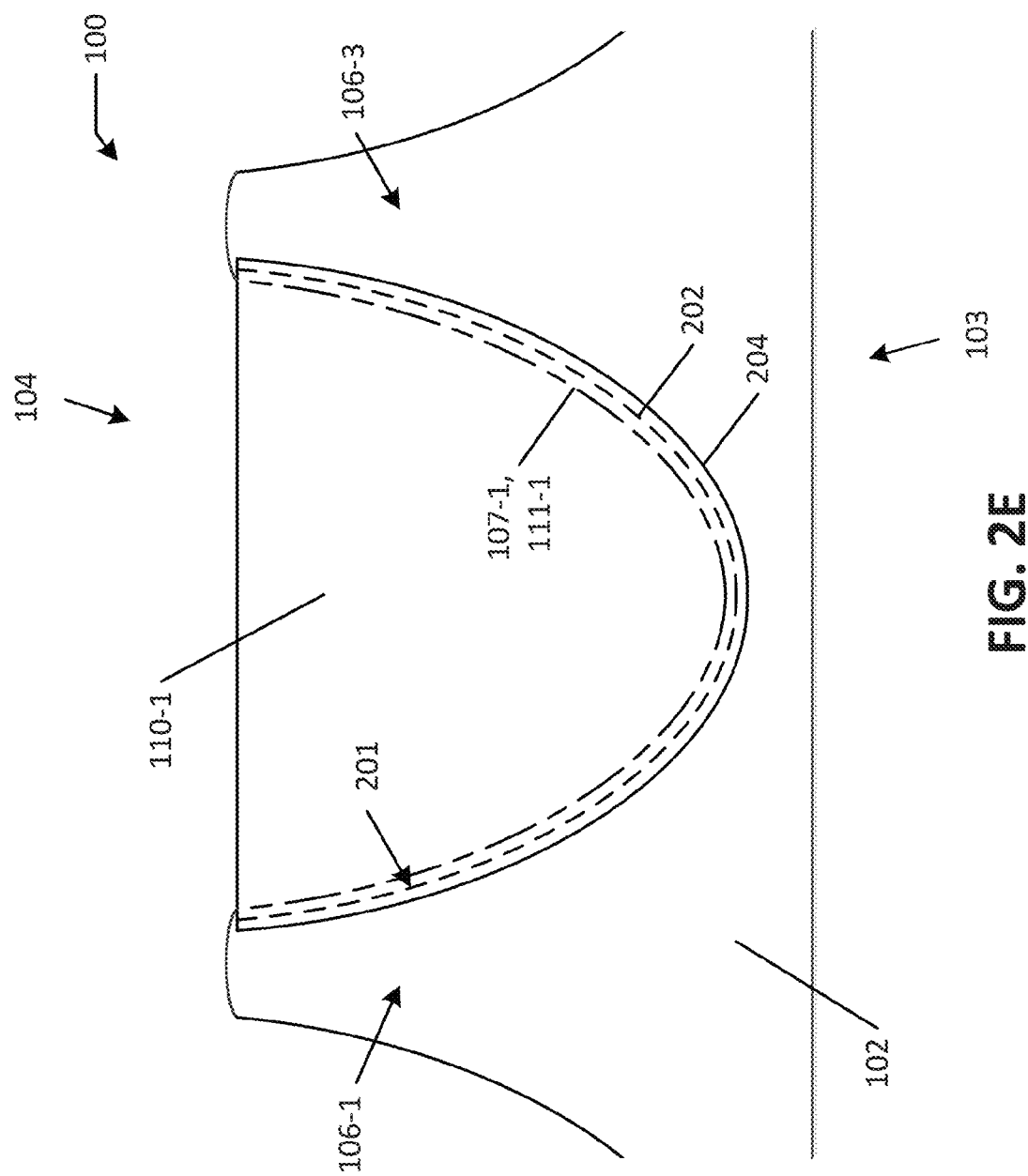

REPLACEMENT HEART VALVES AND THEIR METHODS OF USE AND MANUFACTURE

CROSS-REFERENCE TO RELATED APPLICATIONS

This application is a divisional application of U.S. patent application Ser. No. 14/611,071, filed Jan. 30, 2015, which claims the benefit of and priority to U.S. Provisional Patent Application Ser. No. 61/991,354, filed May 9, 2014, both of which are incorporated by reference herein in their entirety and for all purposes.

FIELD

The subject matter described herein relates generally to improved replacement valves, such as for the aortic and mitral valves of the heart.

BACKGROUND

The human heart has a number of valves for maintaining the flow of blood through the body in the proper direction. The major valves of the heart are the atrioventricular (AV) valves, including the bicuspid (mitral) and the tricuspid valves, and the semilunar valves, including the aortic and the pulmonary valves. When healthy, each of these valves operates in a similar manner. The valve translates between an open state (that permits the flow of blood) and a closed state (that prevents the flow of blood) in response to pressure differentials that arise on opposite sides of the valve.

A patient's health can be placed at serious risk if any of these valves begin to malfunction. Although the malfunction can be due to a variety of reasons, it typically results in either a blood flow restricting stenosis or a regurgitation, where blood is permitted to flow in the wrong direction. If the deficiency is severe, then the heart valve may require replacement.

Substantial effort has been invested in the development of replacement heart valves, most notably replacement aortic and mitral valves. Replacement valves can be implanted percutaneously by way of a transfemorally or transapically introduced catheter, or can be implanted directly through open heart surgery. The replacement valves typically include an arrangement of valve leaflets that are fabricated from porcine tissue or an artificial material such as a polymer. These leaflets are maintained in position by a stent or support structure.

FIG. 1A is a perspective view depicting a prior art prosthetic heart valve 8 of U.S. Pat. No. 7,682,389 ("Beith"). This valve 8 can be implanted directly and includes a stent 10 and three leaflets 30. When implanted, blood is permitted to flow from the upstream (blood inlet) end 14 towards the downstream (blood outlet) end 12, but is prevented from flowing in the reverse direction by the presence of leaflets 30. Leaflets 30 have free edges 34 located on the downstream end 12. Each leaflet 30 also has a fixed edge (or interface) 32 joined with scalloped edge portions 16a, 16b, and 16c, respectively, of stent 10. A cross-sectional plane "I" is shown that bisects the leaflet 30 joined with fixed edge 16a (located at front right). Cross-sectional plane "I" is parallel to the direction of the flow of blood and thus is vertical in FIG. 1A.

FIG. 1B is a side view of a right-side portion of valve 8 after rotation such that plane "I" is aligned with the page. From the reader's perspective FIG. 1B is viewed along a normal to plane "I." From this view, the entirety of fixed edge 32 of leaflet 30 (which is aligned with edge 16a) lies in a flat plane and is straight with no curvature.

FIG. 1C is a side view of a right-side portion of another prior art valve 8 after rotation such that plane "I" is aligned with the page (like the case with FIG. 1B). Here, fixed edge 32 is fully concave from the perspective exterior to valve 8. In the prior art, this fully concave shape was believed to assist in the movement of the leaflet from the open position to the closed position where the leaflet is pushed or draped into the valve interior, as adequate coaptation in the closed state is essential for the proper functioning of the valve.

However, the flat and fully concave shapes of the prior art designs described with respect to FIGS. 1A-1C can lead to a valve with compromised hydrodynamic efficiency due to the fact that the local leaflet length at various heights of the valve is not long enough. This can lead to inadequate valve opening. It can also (or alternatively) lead to local bulging and tightness. The flat or fully concave shapes can both result in localized stress concentrations that, in combination with the aforementioned bulging and tightness, can result in reduced durability and premature failure.

U.S. Pat. No. 6,613,086 ("Moe") describes other variations in the shape of the support structure (or valve body) for a directly implantable valve. Moe describes "an attachment curve" that is defined as the position where the leaflets are coupled along the inner wall of the support structure. Moe seeks to increase the durability of each leaflet coupled to the support structure by moving the leaflet's point of maximum loaded stress along the attachment curve and away from the location of any stress risers. Moe does this by adjusting the radius of the support structure at different heights along the support structure's axis of flow (see numeral 26 of FIG. 1) and at different radial positions within each cross-sectional plane taken perpendicular to and at different heights along the support structure's axis of flow. As a result, Moe's support structures have substantially non-circular or non-cylindrical inner walls along the attachment curve. These support structures can have significantly asymmetric shapes with substantial surface variations, as evidenced by the bulges 58 and 60 described with respect to FIG. 11 of Moe. Moe's support structures are neither cylindrical nor substantially cylindrical as those terms are used herein.

While trying to reduce the localized stress, Moe's approaches lead to local lengthening of the leaflet at that height in the valve. This local lengthening will lead to an increase in the resistance of the leaflet to open and could compromise the full opening of the valve, leading to local bulging in the leaflet surface. This, in turn, will reduce the hydrodynamic efficiency of the valve and potentially reduce the durability of the valve leaflet.

For these and other reasons, needs exist for improved prosthetic valves.

SUMMARY

Example embodiments of improved prosthetic heart valves and their methods of use and manufacture are provided herein. In some of these example embodiments, the prosthetic heart valve can include: a support structure having a central axis oriented in the direction of blood flow through an interior of the support structure; and a plurality of artificial leaflets, each leaflet having a base along the support structure and a free edge allowed to move independent of the support structure. Each leaflet can also have a central axis extending between the base and the free edge. The support structure can be substantially cylindrical where the base of each leaflet meets the support structure. The artificial leaflets can be adapted to move between a first position, for preventing the flow of blood through an interior of the support structure, and a second position, for allowing the flow of blood through the interior of the support structure. For each leaflet, a profile of the base of the leaflet can be at least partially convex when viewed from an exterior of the support structure along a normal to a plane formed by the central axis of the support structure and the central axis of the leaflet. Additional embodiments are also disclosed.

Other systems, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The patent or application file contains at least one drawing executed in color. Copies of this patent or patent application publication with color drawing(s) will be provided by the Office upon request and payment of the necessary fee.

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 1A is a perspective view depicting a prior art prosthetic heart valve.

FIG. 1B is a side view of a right-hand portion of the prior art valve after rotation such that plane "I" is aligned with the page.

FIG. 1C is a side view of a right-hand portion of another prior art valve after rotation such that plane "I" is aligned with the page.

FIG. 2E is an illustrative view depicting a portion of an example embodiment of a prosthetic valve in a laid flat state.

FIGS. 2I-J are perspective views of an example embodiment of a prosthetic heart valve in line drawing and surface shaded forms, respectively.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only and is not intended to be limiting.

Example embodiments of systems, devices, kits, and methods are provided herein that relate to valve replacement in a patient. These embodiments will be described primarily with respect to replacement of the natural aortic heart valve with a prosthetic heart valve having three artificial (i.e., man-made) leaflets. However, the scope of the present disclosure is not limited to such, and can likewise be applied to prosthetics for replacement of other valves of the heart (e.g., mitral) where those prosthetics have two or more leaflets. These prosthetics may also be used to replace valves in other locations in the patient's body outside of the heart.

Figure 2A:
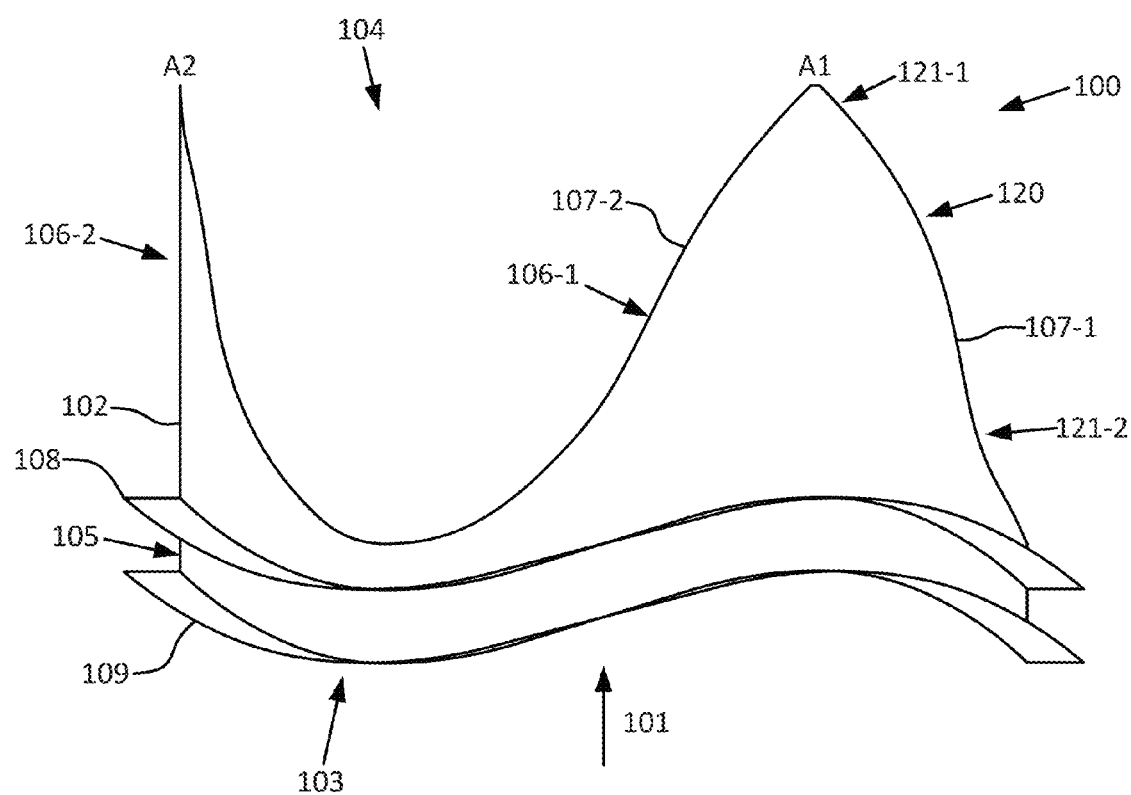
FIGS. 2A-B are perspective views of the front half of an example embodiment of a support structure for a prosthetic heart valve.
Figure 2B:
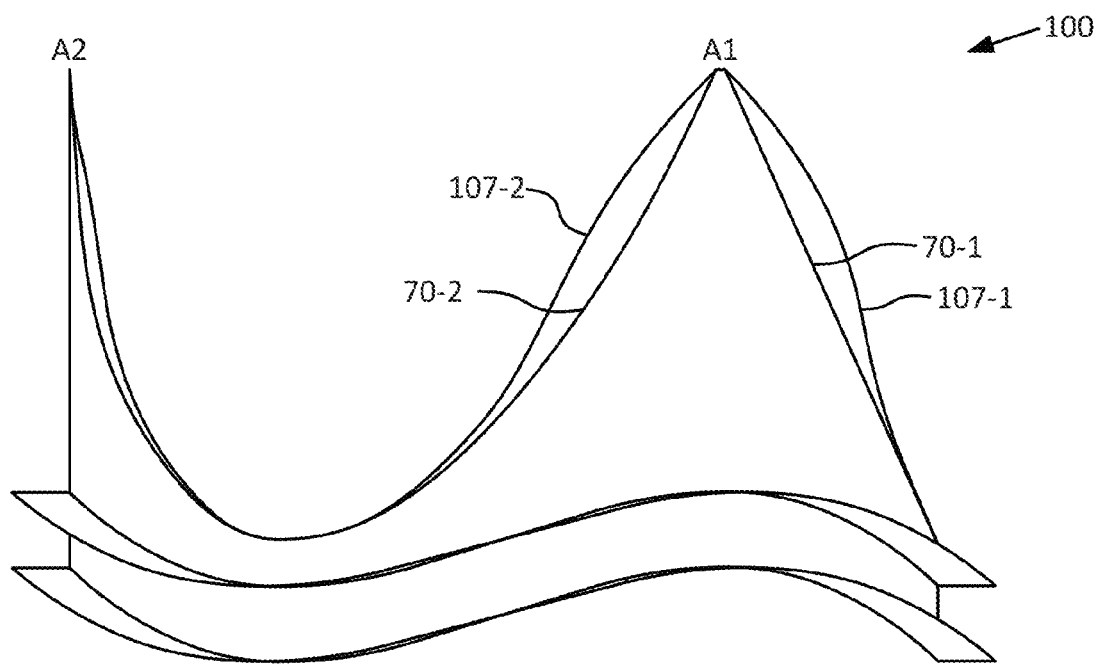
Figure 2C:
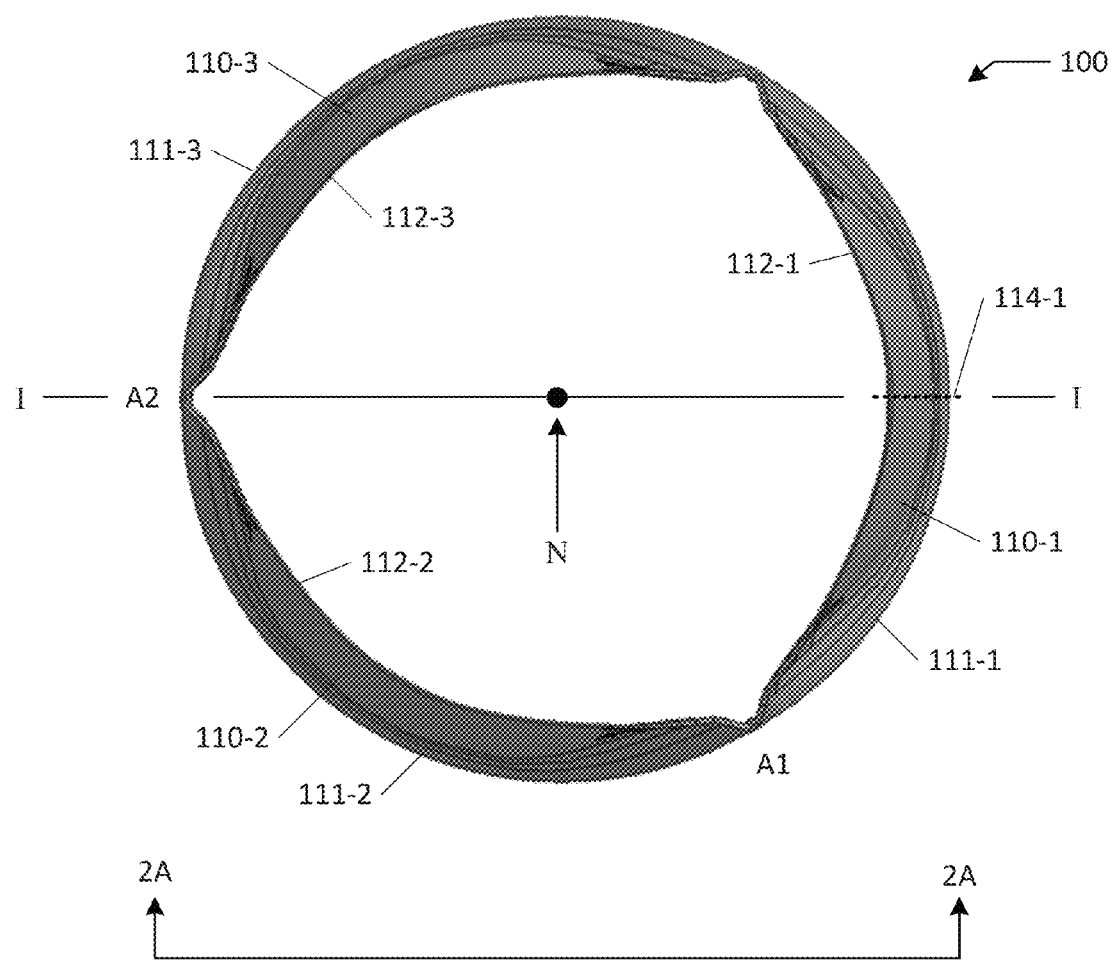
FIGS. 2C-D are top down views of an example embodiment of prosthetic valve leaflets in open and closed states, respectively.
Figure 2D:
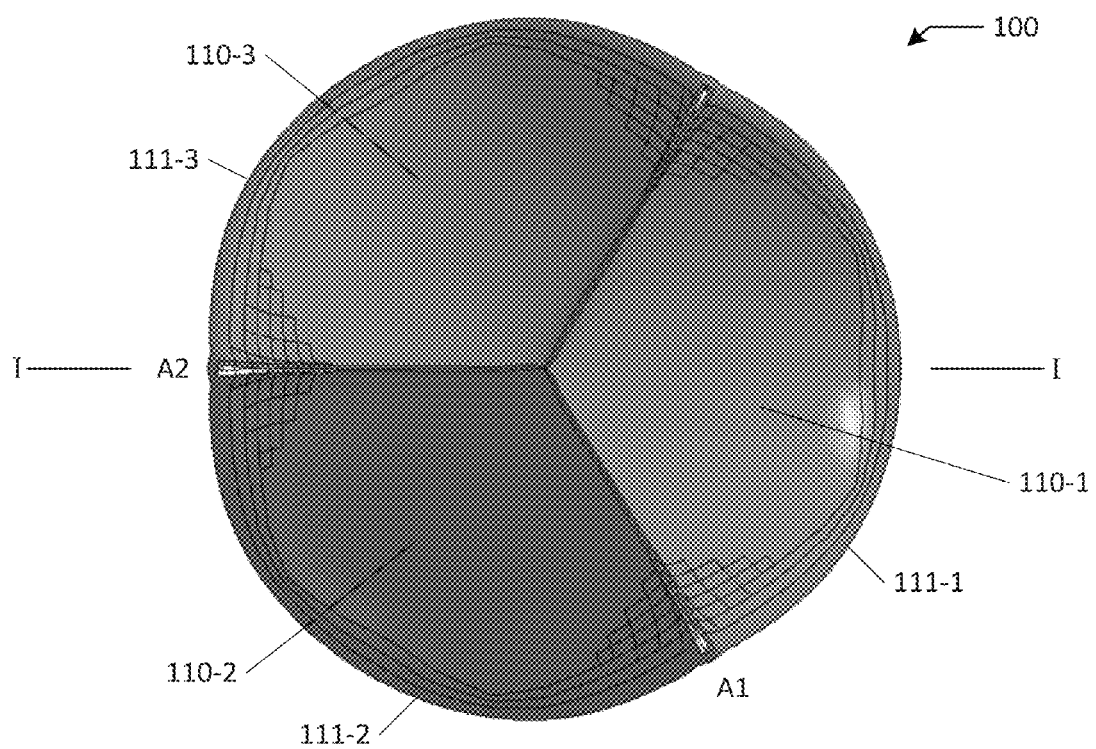

The example embodiments of the prosthetic valves disclosed herein are, in many cases, designed in a manner different from those manners taught by the prior art. FIGS. 2A-B are perspective front views and FIGS. 2C-D are top down views of one such example embodiment of a prosthetic valve 100. Referring to FIG. 2A, a support structure 102 meets a plurality of valve leaflets 110-1, 110-2, and 110-3. Each of leaflets 110 can be discrete from the others (as shown here) or can be portions of one unitary (monolithic) leaflet body.

Support structure 102, which can also be referred to as a stent, is configured to allow blood to flow in direction 101 and has an upstream end 103 and a downstream end 104. Support structure 102 also includes an annular base portion 105 that can have a planar or flat upstream terminus (not shown) or that can have a curved or scalloped upstream terminus as shown here. Support structure 102 also includes three extensions 106 that project from annular base portion 105 towards downstream end 104.

Extensions 106 include curved interfaces 107, which are located directly on an edge in this embodiment. Here, each curved interface 107 is the location where support structure 102 meets the operable base 111 of a leaflet 110. In many embodiments curved interfaces 107 and the leaflet bases 111 will coincide.

In the embodiment depicted in FIG. 2A, support structure 102 is in the form of a base frame. The leaflets can be integrally formed on this base frame 102, such as through a casting (e.g., dip casting) or molding process. A dip casting process that is suitable for formation of the leaflets is described with respect to FIGS. 5A-C. In an example of a dip casting process, the base frame 102 is placed on a mandrel and dipped in a polymer, which results in the formation of leaflets integrated with a polymeric coating over the base frame. Here, curved interfaces 107 refer to the boundary between support structure 102 and each of the integrated leaflets (i.e., base 111 of each leaflet). Depending on the particular implementation, curved interfaces 107 can coincide with the downstream edge of the base frame itself or the downstream edge of the coating over the base frame.

In some embodiments, leaflets 110 (whether they be tissue or artificial) can be physically joined to support structure 102 through a coupling process such as sewing. FIG. 2E is an illustration of an example embodiment of a portion of valve 100 in a laid flat state. Here, leaflet 110-1 has been coupled to support structure 102 by a seam 201 created by sewing a suture 202 through leaflet 110-1 and support structure 102. The physical base edge 204 of leaflet 110 can be located upstream from seam 201 (as shown), folded back into a location downstream of seam 201, or otherwise. In these embodiments, both curved interface 107-1 and base 111-1 refer to the transition between the secured portion of leaflet 110-1 and the operable portion of leaflet 110-1 that is free to transition or deflect between the open and closed states, which in the embodiment of FIG. 2E coincides with the upstream edge of support structure 102.

Referring back to FIG. 2A, annular base portion 105 also includes flanges 108 and 109 between which a sewing cuff (not shown) can be placed. As an alternative for all of the embodiments described herein, only a single flange 108 may be present, or the flanges 108 and 109 can be omitted altogether. In light of this description, those of ordinary skill in the art will readily understand the design and appearance of a sewing cuff and how it can be coupled with one or more flanges of support structure 102.

In FIG. 2A, support structure 102 is positioned according to the perspective depicted by line 2A-2A of FIG. 2C. Stated differently, cross-sectional plane "I" of FIG. 2C is parallel to the page of FIG. 2A such that the viewer views FIG. 2A along a normal "N" to plane "I". Plane "I" can also be described as extending through a central axis of valve 100 oriented in the direction of blood flow (indicated by the solid circle at the tip of the normal "N" arrow in FIG. 2C) and a central axis of the respective leaflet extending between base 111 and free edge 112. An example of the central axis 114-1 is where plane "I" intersects leaflet 110-1 in FIGS. 2C-D. There, plane I is a center plane or mid-plane to leaflet 110-1.

FIG. 2B depicts the embodiment of FIG. 2A in an annotated form to allow comparison with the flat downstream edges 70-1 and 70-2 that would be present if support structure 102 was shaped according to the prior art approach of FIGS. 1A-B. Here, interfaces 107-1 and 107-2 can be seen to bulge in a pronounced fashion from flat edges 70-1 and 70-2. Note that edge 70-2 is referred to as flat because it would appear flat if support structure 102 were rotated to place edge 70-2 in the position of edge 70-1 in FIG. 2B. The bulges of interface 107-1 and 107-2 would be even more pronounced if compared to the prior art concave edge approach of FIG. 1C. Although interface 107-3 and 70-3 are not shown, the same relationships would present for those as well.

FIG. 2C depicts leaflets 103 in their open positions with support structure 102 omitted. However, were support structure 102 to be shown, apex A1 of extension 106-1 and apex A2 of extension 106-2 (both shown in FIG. 2A) would be positioned as noted in FIG. 2C.

Leaflets 103 each have a free edge 112 that moves independent of support structure 102. FIG. 2D depicts leaflets 110 after movement to their closed positions. In the closed position, in many embodiments the majority of free edges 112 will be in contact with each other. In some embodiments, the entirety of free edges 112 will be in contact with each other.

As seen in FIG. 2A, interface 107-1 is partially convex and concave from the perspective exterior to valve 100. Interface 107-1 coincides with base 111-1 of leaflet 130-1 (see FIGS. 2I-K). The convex portion 120 is midway along interface 107-1. Convex portion 120 is convex in two dimensions, e.g., like a portion of the border of a two-dimensional ellipse from the perspective of outside the ellipse.

Concave portions 121-1 and 121-2 can be present on both sides of the convex middle portion 120. As seen in FIG. 2A, concave portion 121-1 has a significantly lower degree of curvature than convex middle portion 120. The combination of a convex portion with one or more concave portions gives interface 107-1 an undulating appearance when viewed from this perspective. This appearance can also be referred to as S-shaped or multi-curved if there is at least one concave portion and at least one convex portion (e.g., two concave portions and two convex portions qualifies as S-shaped), and those portions can vary in height and degree of curvature. In some embodiments, interface 107-1 can be convex along its entire height (or length). In other embodiments, interface 107-1 can include a convex portion with a flat (or linear) portion on one or both sides. In still other embodiments, interface 107-1 can include a convex portion in combination with any number of flat portions and concave portions.

Figure 2F:
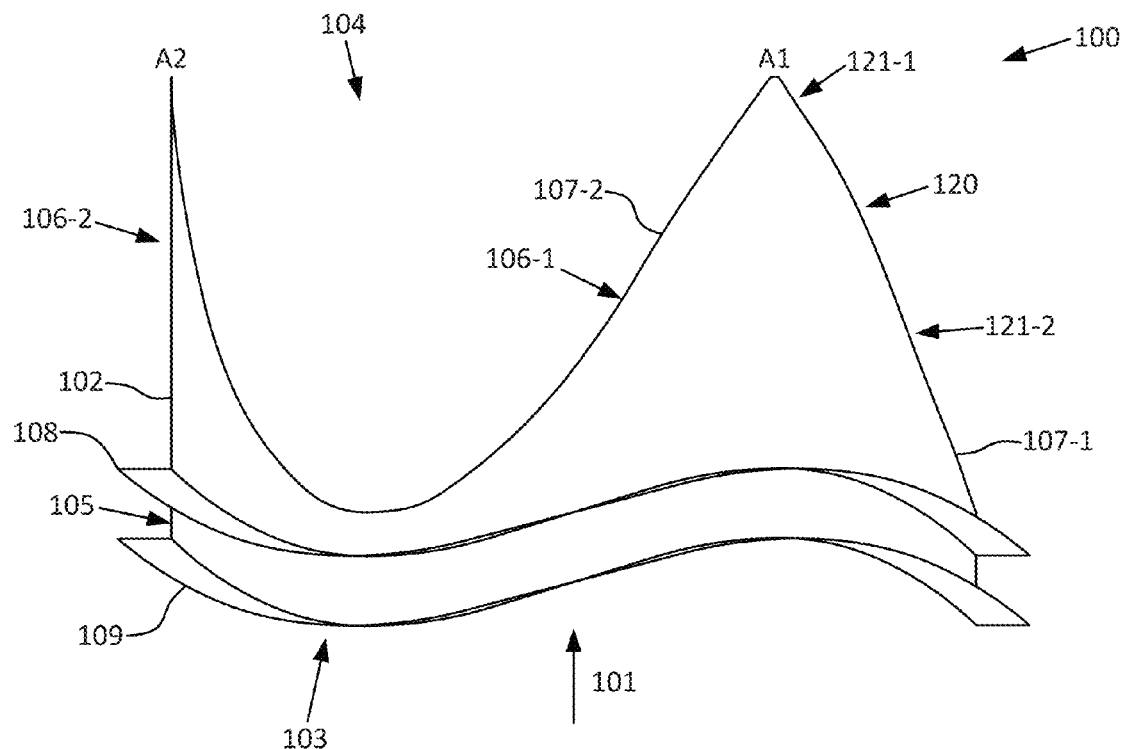
FIGS. 2F-H are perspective views of an example embodiment of a prosthetic heart valve.
Figure 2G:
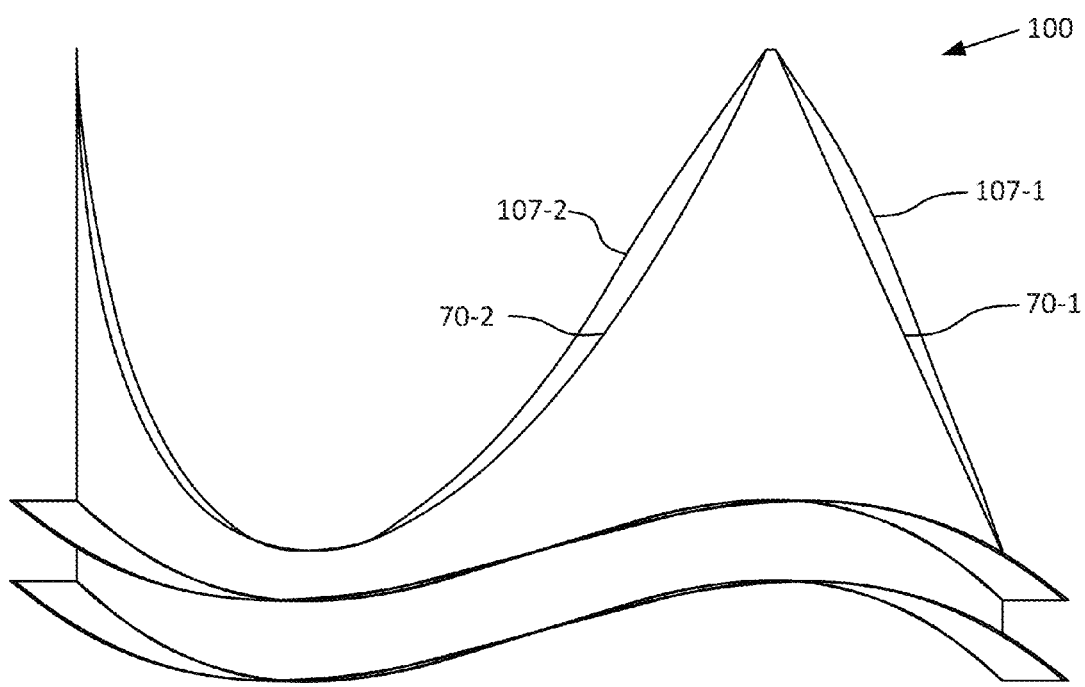

FIG. 2F is a perspective front view of another example embodiment of a support structure 102 for a prosthetic valve 100. In this embodiment, the degree of curvature present in convex portion 120 and concave portions 121-1 and 121-2 is relatively less than in the embodiment described with respect to FIG. 2A. FIG. 2G is a perspective front view of the embodiment of FIG. 2F annotated to allow comparison of interfaces 107-1 and 107-2 with prior art edges 70-1 and 70-2 (described with respect to FIG. 2B).

Figure 2H:
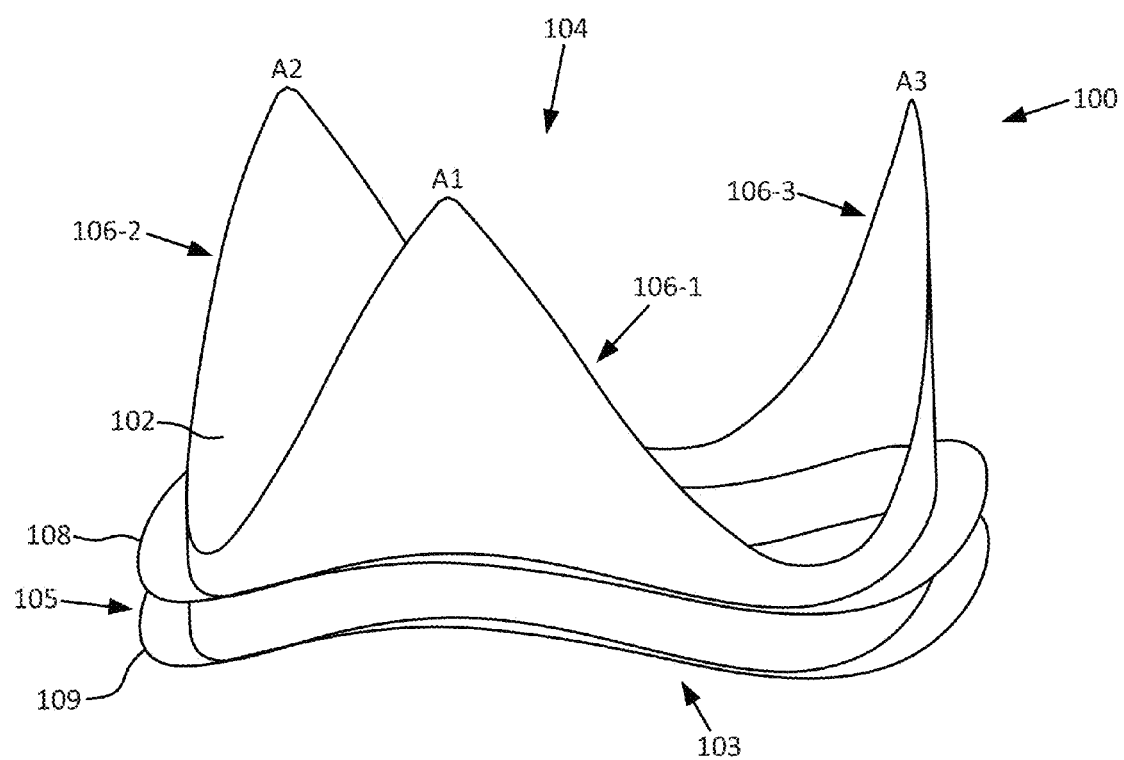
Figure 21:
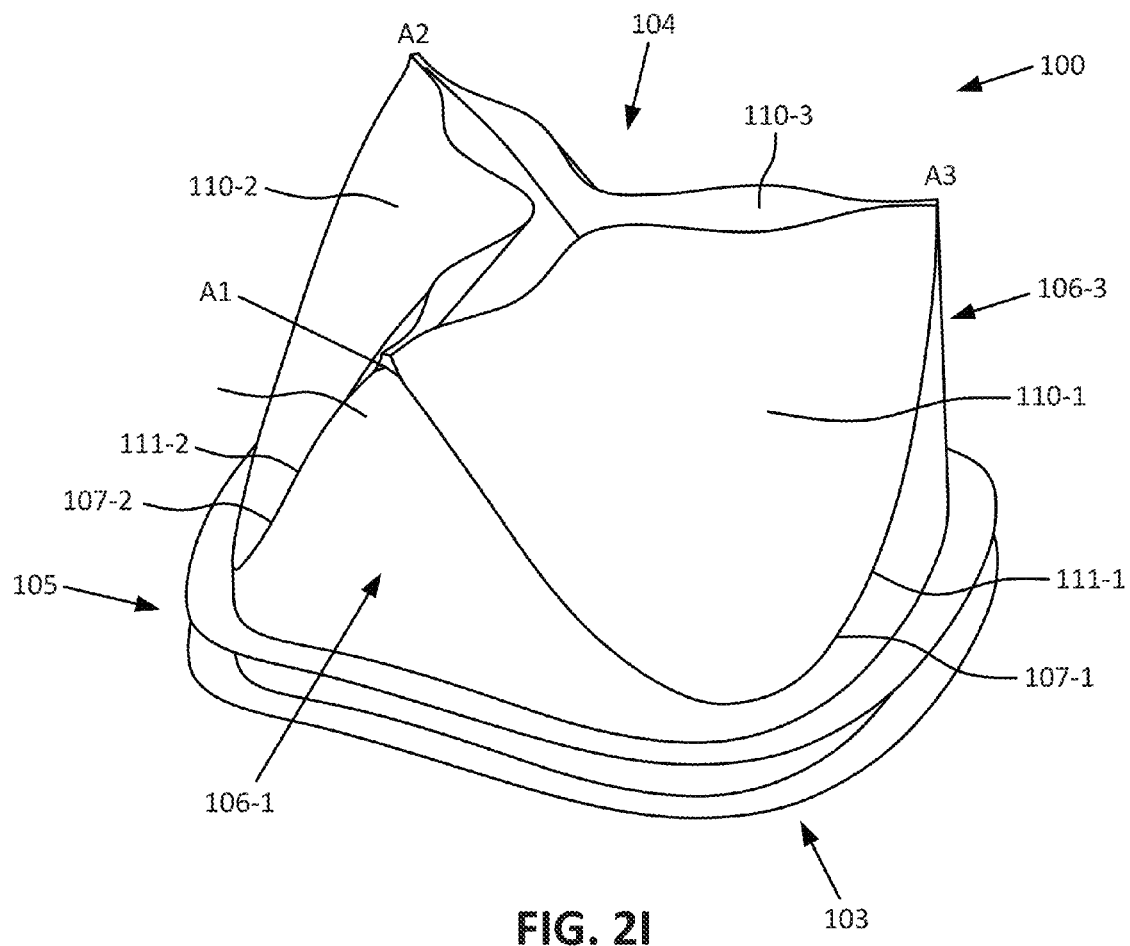
Figure 2J:
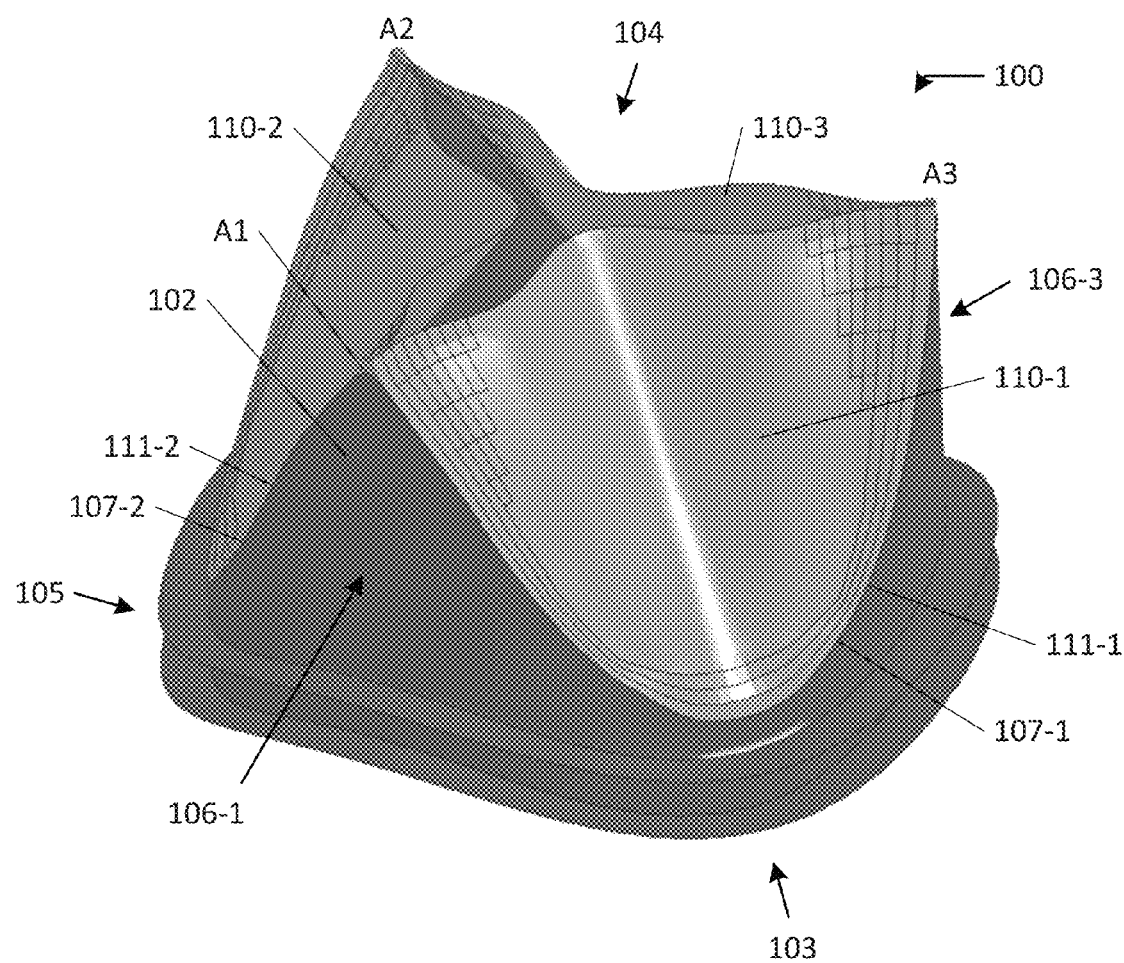
Figure 2K:
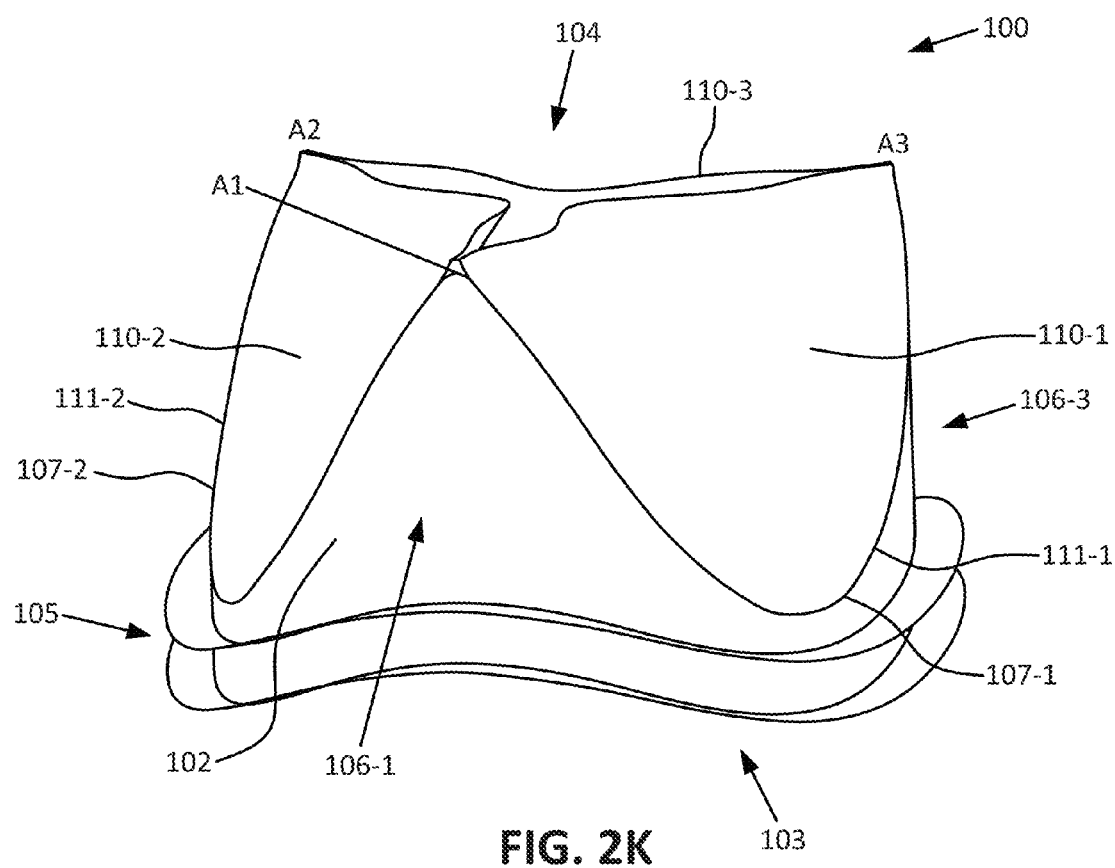
FIG. 2K is a perspective view of an example embodiment of a prosthetic heart valve.

In FIGS. 2F-G, only the front half of support structure 102 is shown (i.e., forward of plane "I"), with the back half and valve leaflets 110 omitted for ease of illustration. The entire support structure 102 is depicted in the perspective view of FIG. 2H. FIGS. 2I-2J are a line drawing perspective view and surface shaded perspective view, respectively, of the embodiment of FIG. 2F with leaflets 110 included. FIG. 2K is a line drawing perspective view of the embodiment of FIG. 2F taken from a different perspective than that of FIG. 2I.

In addition to being described as "convex," certain convex portions of interface 107-1 can be described as tapering at an increasing rate as the distance increases from upstream end 103. Characterized in yet another manner, the convex curve may be regarded as "concave down" with respect to a straight line reference similar to edge 70-1 described with respect to FIG. 2B. The convexity may change in direction to "concave up" (i.e., change in mathematical sign considering a second derivative of interface 107-1) and/or may change in magnitude (i.e., in terms of degree of curvature) along the length of interface 107-1.

For all of the embodiments described herein, any of the aforementioned shapes can likewise be present on interfaces 107-2 and 107-3 when those interfaces 107-2 and 107-3 are viewed from the same perspective as interface 107-1 in FIG. 2A. Preferably, each of interfaces 107-1, 107-2 and 107-3 has the same shape to maximize the synchronous motion of leaflets 110, as significantly asynchronous motion can negatively impact the durability of valve 100. However, each interface 107 can vary in shape with respect to the others provided that the durability of valve 100 remains acceptable.

While support structure 102 can take various shapes, in all embodiments, support structure 102 can be substantially cylindrical or cylindrical. As those of ordinary skill in the art understand, being "cylindrical" does not require support structure 102 to be in the form of a full geometric cylinder (e.g., vertical walls oriented at a right angle to a circular cross-section), but rather requires support structure 102 to lie along a part of a hypothetical geometric cylinder (with only minor deviation). For example, the entire inner lumen surface (the surface directly adjacent the flow of blood) of support structure 102 as depicted in FIG. 2D is cylindrical as that term is used herein. Similarly, those of ordinary skill in the art understand that a support structure 102 that is "substantially cylindrical" is permitted greater deviation from a mathematical cylinder than simply "a cylindrical support structure" and would readily recognize those support structures that qualify as being substantially cylindrical.

While the entirety of support structure 102 can be cylindrical or substantially cylindrical, it is also the case that only part of support structure 102 can be cylindrical or substantially cylindrical, with the remaining part of support structure 102 being non-cylindrical. For instance, in the embodiment described with respect to FIG. 2D, although the entire inner lumen surface of support structure 102 is cylindrical, the opposite outer surface has flanges 108 and 109 that are not cylindrical.

In other embodiments, only the portion of support structure 102 along curved interfaces 107 (e.g., along base 111 of leaflets 110) may be cylindrical or substantially cylindrical. Such a configuration distinguishes over the subject matter of U.S. Pat. No. 6,613,086 ("Moe") described herein.

When support structure 102 is formed from a base frame coated in polymer, then in some embodiments, only the base frame (either the entirety or a portion thereof) can be cylindrical or substantially cylindrical, while the outer surface of the polymer coating is not cylindrical or not substantially cylindrical. For example, in some embodiments the inner lumen surface of a base frame is cylindrical and the outer surface of the polymer coating (along the inner lumen of the base frame) is substantially cylindrical (or even non-cylindrical) due to variations in the coating thickness.

In the embodiments of FIGS. 2A-B and 2F-K, valve 100 is sized to fit a 23 millimeter (mm) aortic tissue annulus, although this embodiment can be sized at other standard dimensions as well, such as 17 mm, 18 mm, 19 mm, 20 mm, 21 mm, 22 mm, 24 mm, 25 mm, 26 mm, 27 mm, 28 mm, and 29 mm, as well as dimensions that lie in between. These dimensions are commonly referred to as the inner diameter or "ID" of valve 100, which is the lateral dimension of the valve at a position commensurate with leaflets 110. The valve may have an even larger lateral dimension elsewhere, such as the location of the sewing cuff.

Figure 4A:
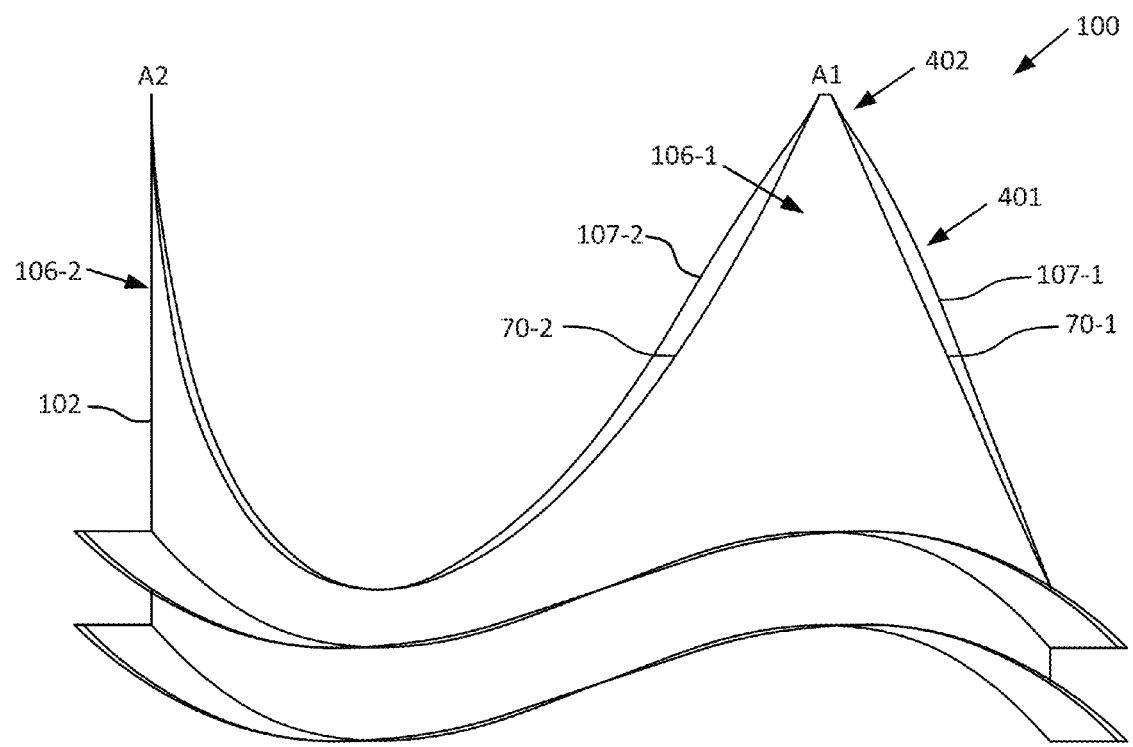
FIGS. 4A-B are perspective views depicting the front half of additional example embodiments of a support structure.

FIG. 4A depicts another embodiment of valve 100 (in a view similar to that of FIG. 2A). In this embodiment, valve 100 is sized for a 19 mm tissue annulus. Interface 107-1 includes a convex portion 401 with a smaller flat or concave portion 402 near apex A1 of extension 106-1. Interface 107-1 of valve 100 can again be seen to bulge in a pronounced convex fashion from the overlaid flat edge 70-1. Interface 107-2 and 107-3 (not shown) have similar shapes.

Figure 4B:
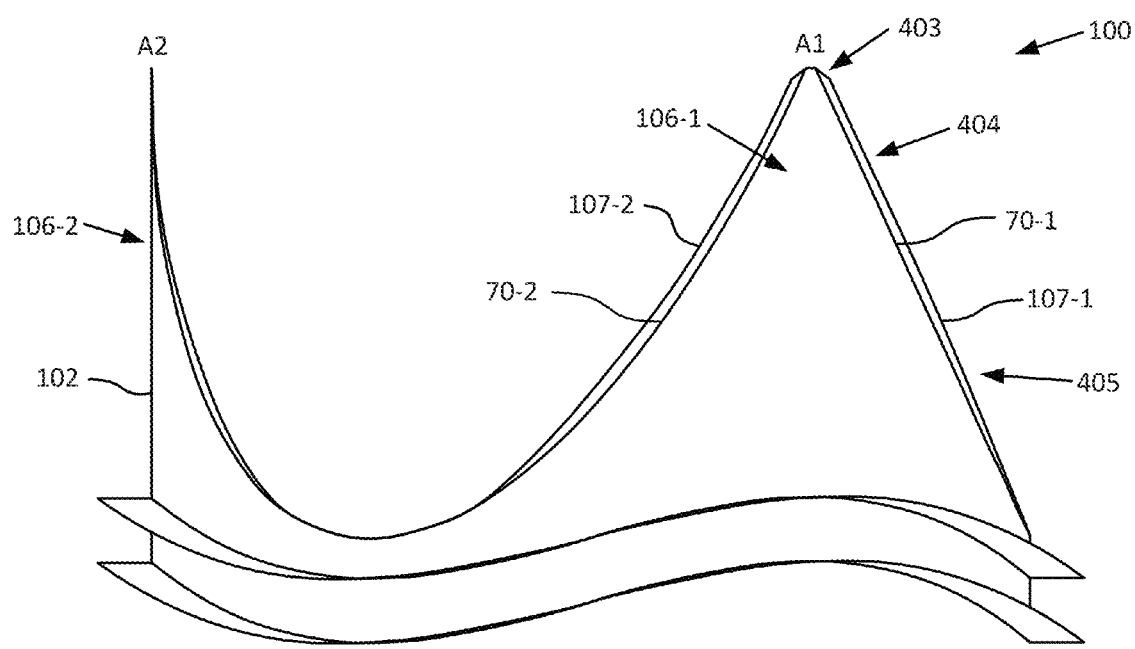

FIG. 4B depicts another embodiment of valve 100 (again in a view similar to that of FIG. 2A). In this embodiment, valve 100 is sized for a 27 mm tissue annulus. Interface 107-1 is S-shaped with a first slightly convex portion 403 adjacent apex A1, a concave portion 404 immediately upstream (below), and a second slightly convex portion 405 upstream from (below) concave portion 404. Overlaid flat edge 70-1 is again present to further illustrate the differences with interface 107-1 of this embodiment of valve 100. Interface 107-2 and 107-3 (not shown) have similar shapes.

The embodiments of valve 100 described herein are suitable for implantation in the body of a patient using any number of medical procedures. Preferably, these embodiments of valve 100 are for direct implantation to the aortic annulus using open heart surgery. Such embodiments of valve 100 are not radially collapsible for insertion into an intravascular delivery device (e.g., a catheter) or a transapical delivery device. However, in other embodiments, valve 100 can be configured with a radially collapsible support structure 102 that allows the lateral dimension of valve 100 to be reduced by a degree sufficient to permit the insertion into an appropriately sized intravascular or transapical delivery device.

All of the embodiments of valve 100 described herein can also be provided to a medical professional (or retained by a medical professional) as part of a kit (or a set) of prosthetic valves being sized for various tissue annulus dimensions. The sizes can include any combination of two or more of the following: 17 mm, 18 mm, 19 mm, 20 mm, 21 mm, 22 mm, 23 mm, 24 mm, 25 mm, 26 mm, 27 mm, 28 mm, and 29 mm. In one embodiment, the kit includes at least one valve 100 configured with an at least partially convex interface 107 as described herein, along with one or more valves having different configurations. In another embodiment, for each labeled size, the kit includes at least one of the embodiments of a valve 100 described herein. In still another embodiment, the kit includes a 19 mm valve 100 in the form of the embodiment described with respect to FIG. 4A, a 23 mm valve 100 in the form of the embodiment described with respect to FIG. 2F, and a 27 mm valve 100 in the form of the embodiment described with respect to FIG. 4B.

Support structure 102 can be fabricated from any desired material, such as polymers (e.g., polyether ether ketones (PEEK), polyurethanes, etc.), metals (e.g., nitinol, stainless steel, etc.), and others. Leaflets 110 are fabricated from an artificial polymeric material, including any biostable polyurethanes and polyurethane compositions (e.g., polysiloxane-containing polyurethanes, etc.) known in the art. Examples of polyurethane containing leaflets are described in U.S. Pat. No. 6,984,700, U.S. Pat. No. 7,262,260, U.S. Pat. No. 7,365,134, and Yilgor et al., "Silicone containing copolymers: Synthesis, properties and applications," Prog. Polym. Sci. (2013), all of which are incorporated by reference herein in their entirety for all purposes. Materials that approach ideal isotropic non-creeping characteristics are particularly suitable for use in many embodiments. While many materials can be used, it is preferable that the selected material have the appropriate modulus of elasticity to allow leaflets 110 to readily and repeatedly transition between the open and closed states without succumbing to fatigue or stress related failure. In many example embodiments, the modulus of elasticity for leaflets 110 is in the range of 10-45 MegaPascals (MPa). In certain other example embodiments, the modulus of elasticity for leaflets 110 is in the range of 20-30 MPa.

Figure 3A:
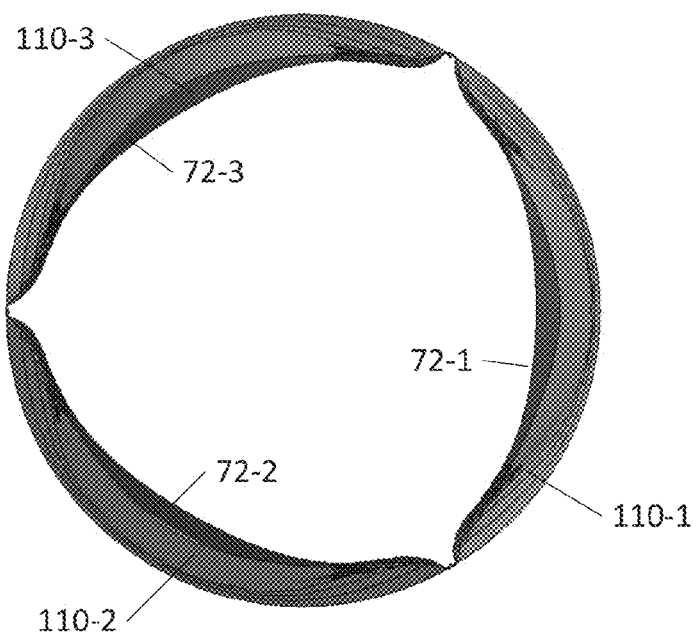
FIG. 3A is a color top down view comparing the positions of two sets of leaflets in their open states, where the support structure is not shown.
Figure 3B:
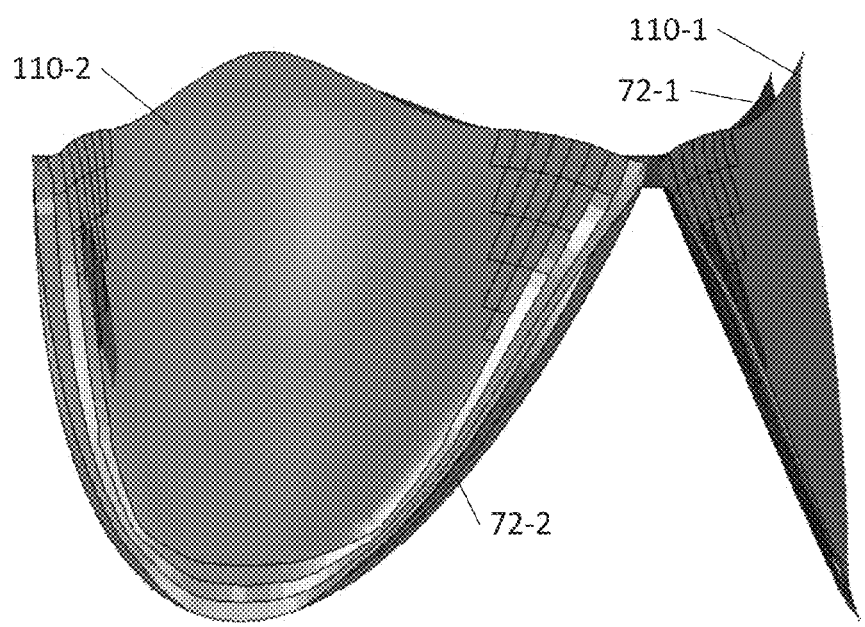
FIG. 3B is a color perspective view comparing the positions of two sets of leaflets in their open states within the front half of a prosthetic heart valve where the support structure is not shown.

Valves 100 designed in accordance with the embodiments described herein exhibited superior performance over previous valves in a number of respects. For example, FIGS. 3A-N are a series of simulation outputs that compare the performance of leaflets of an embodiment of a 23 mm valve 100 having leaflets 110 (similar to that described with respect to FIGS. 2F-K) as compared to a valve having a flat edge 70 with leaflets 72 similar to the prior art approach described with respect to FIGS. 1A-B as well as FIGS. 2B, 2G, and 4A-B. Such comparisons demonstrate the improved performance of the at least partially convex edge embodiments over the prior art flat edge approach (as well as the prior art concave edge approach described with respect to FIG. 1C).

FIG. 3A is a top down view of leaflets 110 (blue) in their open position as compared to leaflets 72 (red) each having a base that would be attached to flat edge 70. It is seen here that the free edges of leaflets 110 approach the wall of support structure 102 (not shown) much more closely than the free edges of leaflets 72 and thus provide significantly less resistance to blood flow through the interior of valve 100. This is shown further in FIG. 3B, which is a view of open leaflets 110 in an orientation corresponding to that of FIG. 2F but without showing support structure 102. The visible surfaces are those that are closest to the viewer. Almost the entirety of leaflets 110 are closer to the viewer than leaflets 72, resulting in a larger interior space through which blood can flow.

Figure 3C:
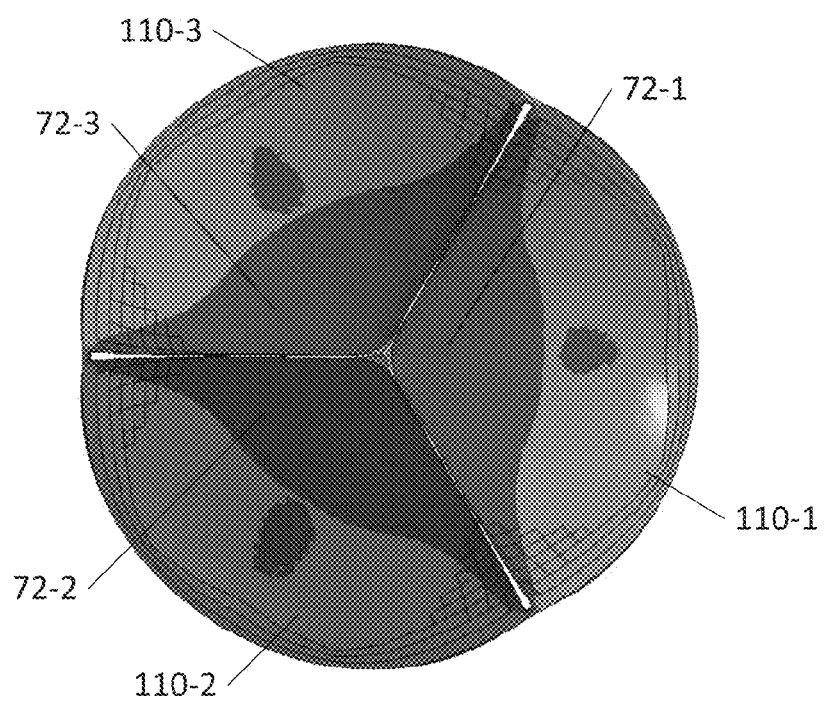
FIG. 3C is a color top down view comparing the positions of two sets of leaflets in their closed states, where the support structure is not shown.
Figure 3D:
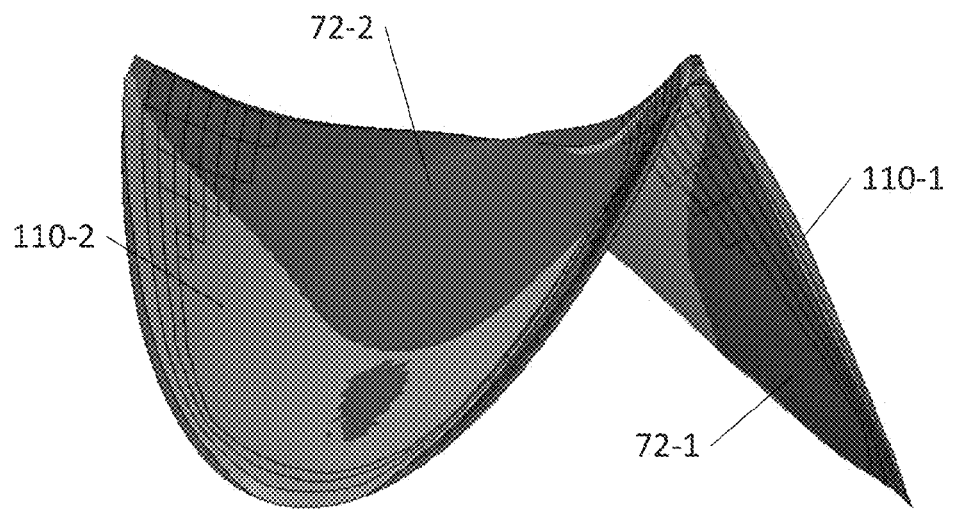
FIG. 3D is a color perspective view comparing the positions of two sets of leaflets in their closed states within the front half of a prosthetic heart valve where the support structure is not shown.

FIG. 3C is a top down view of leaflets 110 (blue) in their closed position as compared to leaflets 72 (red). Visible surfaces indicate those that are closest to the viewer looking into valve 100 from the downstream end. Leaflets 110 extend further into the interior of valve 100 than leaflets 72, and achieve a higher degree of coaptation and thus a better seal against backflow and regurgitation, particularly in the center where all three of leaflets 110 meet. Leaflets 110 also eliminate the buckled or dimpled portion that is present in each of leaflets 72 and seen as the circular spots. Leaflets 110 of FIG. 3C is shown from a different perspective in FIG. 3D.

Figure 3E:
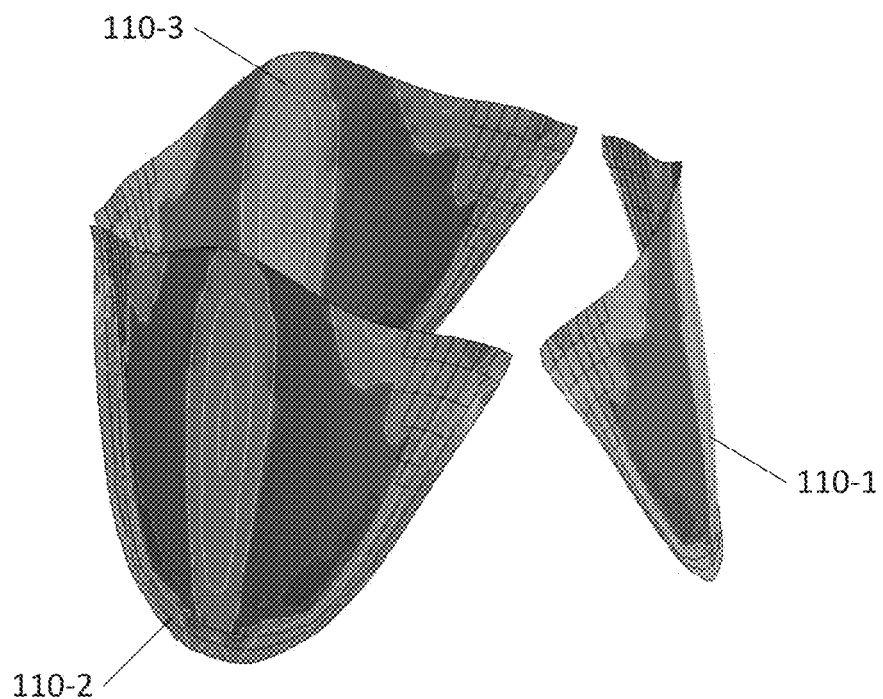
FIG. 3E is a color perspective view depicting an example embodiment of leaflets in their open state with the stress levels experienced at various positions across the surface of the leaflets, where the support structure is not shown.
Figure 3F:
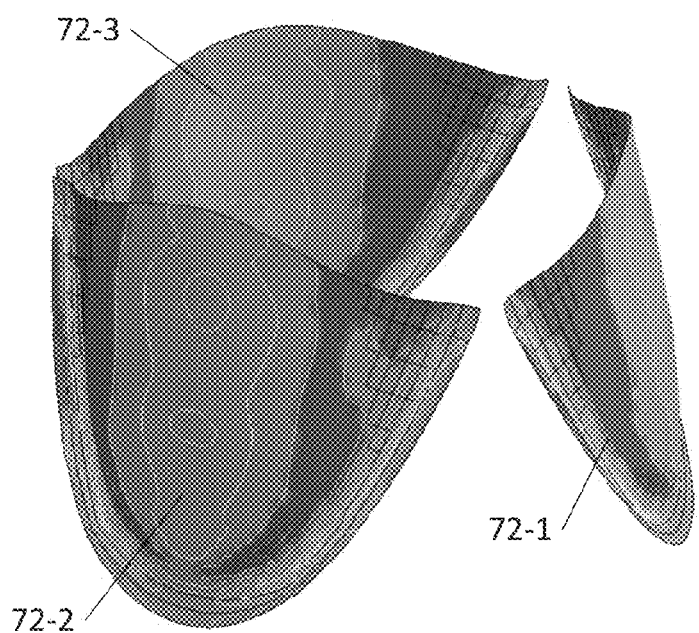
FIG. 3F is a color perspective view depicting conventional leaflets in their open state with the stress levels experienced at various positions across the surface of the leaflets, where the support structure is not shown.

FIG. 3E is a perspective of leaflets 110 in the open position showing the stress levels experienced at various positions across the surface of leaflets 110. In FIGS. 3E-N, increasing relative stress is indicated by color in the following order: dark blue (lowest relative stress), light blue, green, yellow, orange, and red (highest relative stress). The maximum principal stress experienced by leaflets 110 was calculated to be 2.64 (MPa). This is compared to leaflets 72 of FIG. 3F, which is shown on the same scale as FIG. 3E and indicates that leaflets 72 generally experience higher stress, particularly across the center region of leaflets 72 and along the mid-region of the bases. The maximum principal stress experienced by leaflets 72 was calculated to be 2.75 MPa.

Figure 3G:
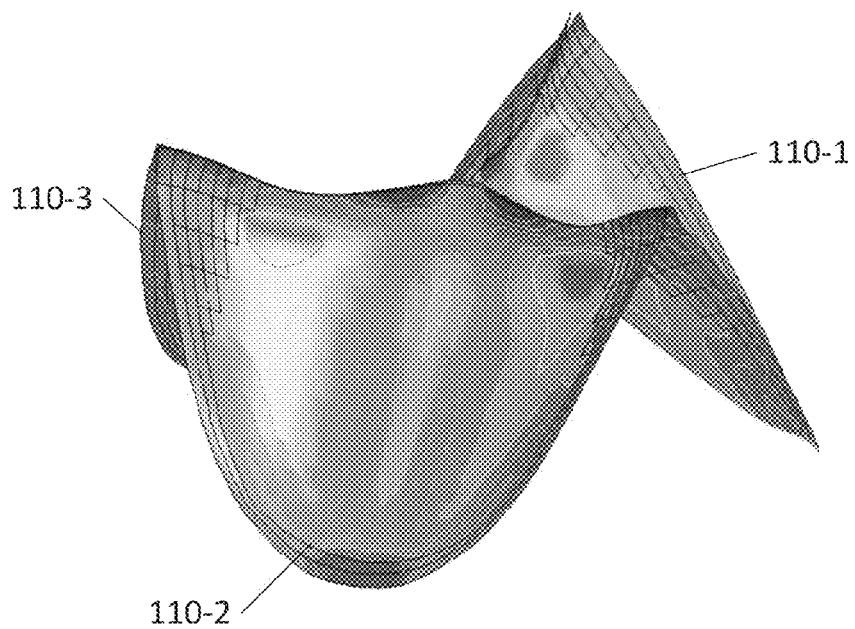
FIG. 3G is a color perspective view depicting an example embodiment of leaflets in their closed state with the stress levels experienced at various positions across the surface of the leaflets, where the support structure is not shown.
Figure 3H:
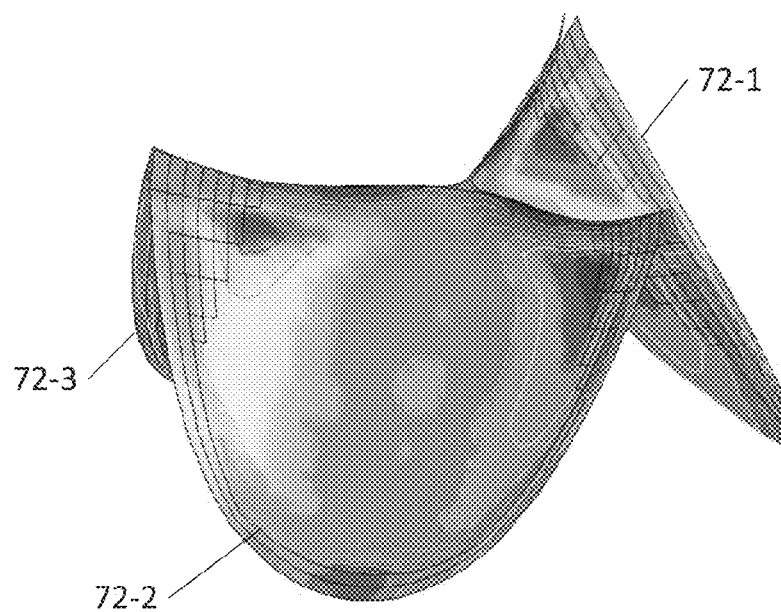
FIG. 3H is a color perspective view depicting conventional leaflets in their closed state with the stress levels experienced at various positions across the surface of the leaflets, where the support structure is not shown.

FIG. 3G is a perspective of leaflets 110 in the closed position showing the stress levels experienced at various positions across the surface of leaflets 110. The maximum principal stress experienced by leaflets 110 in this position was calculated to be 2.75 MPa. FIG. 3H, which is shown on the same scale as FIG. 3G, indicates that leaflets 72 experience higher stress in pockets positioned on both sides of each leaflet 72 near the junction of the free edge and base. The maximum principal stress for leaflet 72 was 3.005 MPa, which is again higher than for leaflets 110.

Figure 3I:
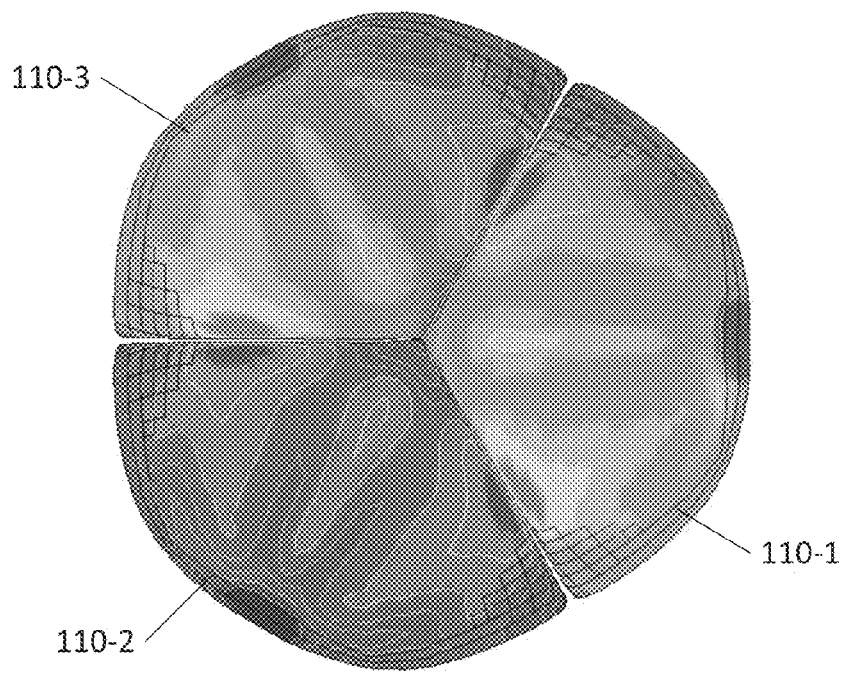
FIG. 3I is a color top down view depicting an example embodiment of leaflets in their closed state with the stress levels experienced at various positions across the surface of the leaflets, where the support structure is not shown.
Figure 3J:
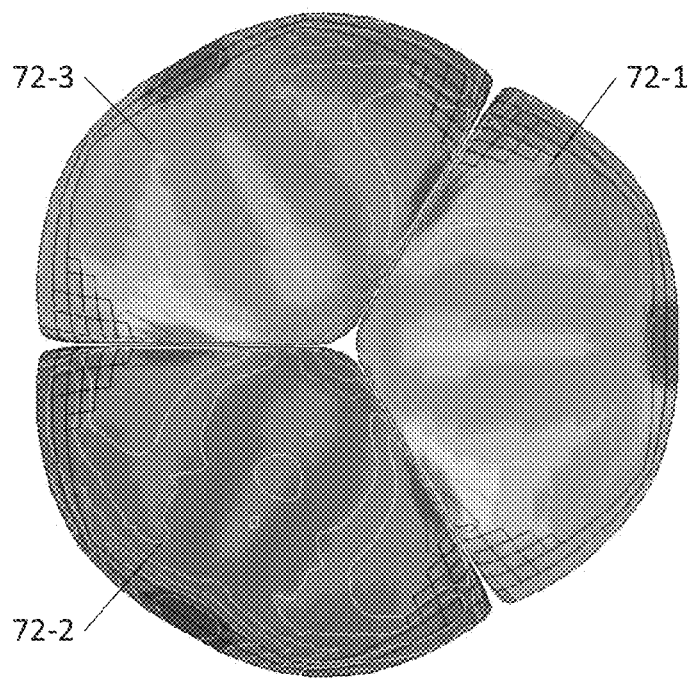
FIG. 3J is a color top down view depicting conventional leaflets in their closed state with the stress levels experienced at various positions across the surface of the leaflets, where the support structure is not shown.

FIG. 3I is a top down view of the simulation of leaflets 110 in FIG. 3G and FIG. 3J is a top down view of the simulation of leaflets 72 in FIG. 3H. This comparison shows the higher degree of coaptation achieved by leaflets 110, particularly at the center of valve 100 and where adjacent free edges meet in proximity to the support structure (not shown).

Figure 3K:
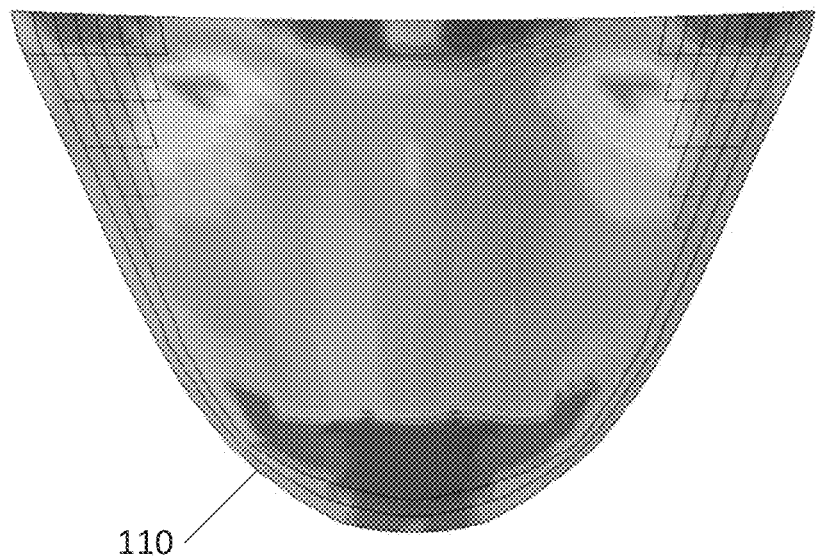
FIG. 3K is a color frontal view depicting an example embodiment of a leaflet mapped with the simulated relative degree of vertical strain energy release.
Figure 3L:
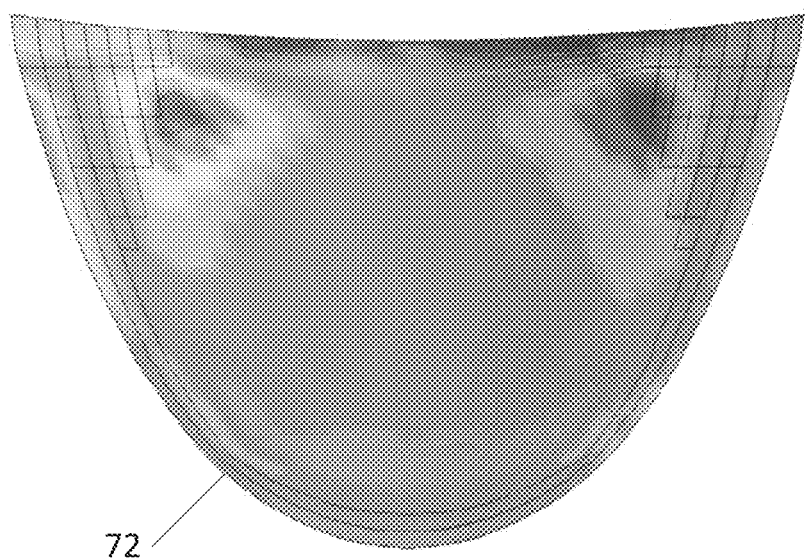
FIG. 3L is a color frontal view depicting a conventional leaflet mapped with the simulated relative degree of vertical strain energy release.
Figure 3M:
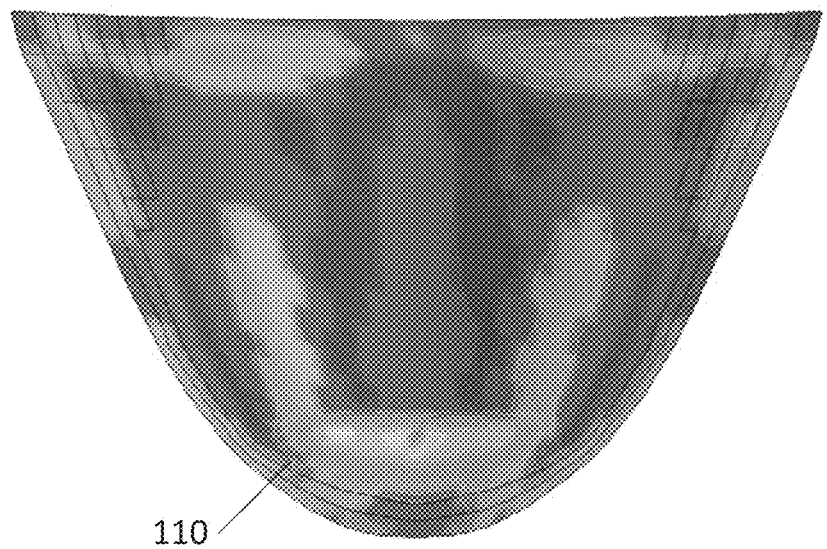
FIG. 3M is a color frontal view depicting an example embodiment of a leaflet mapped with the simulated relative degree of lateral strain energy release.
Figure 3N:
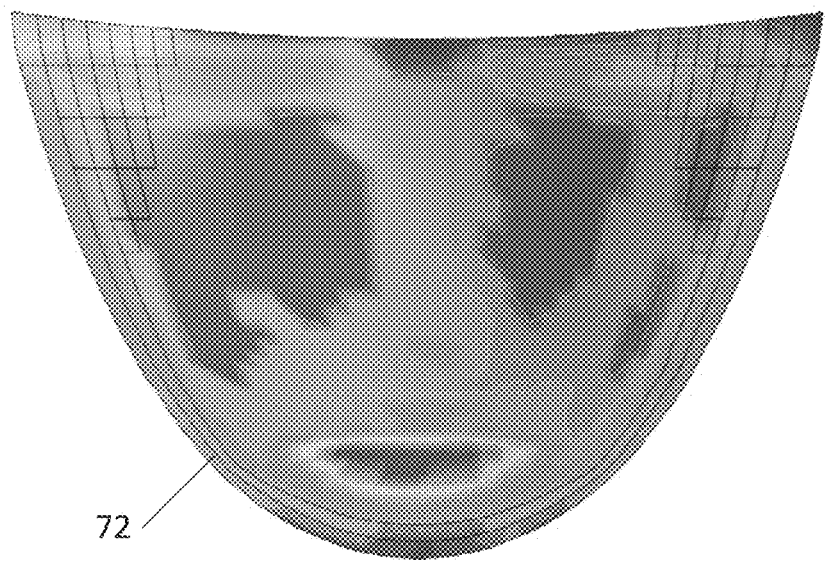
FIG. 3N is a color frontal view depicting a conventional leaflet mapped with the simulated relative degree of lateral strain energy release.

FIG. 3K is a front view of leaflet 110 mapped with the simulated relative degree of vertical strain energy release. FIG. 3L is a front view of leaflet 72 showing the simulated relative degree of vertical strain energy release according to the same scale as FIG. 3K. FIG. 3M is a front view of leaflet 110 mapped with the simulated relative degree of lateral strain energy release. FIG. 3N is a front view of leaflet 72 showing the simulated relative degree of lateral strain energy release according to the same scale as FIG. 3M.

Strain energy release is determined by an integral across the entire cycle of motion of the leaflet, i.e., movement between the open and closed positions and back. Vertical strain energy release is a measurement of how much energy is present at each position on the leaflet to drive the growth of a defect in the vertical direction, i.e., between bottom and top as shown in FIGS. 3K-L. Lateral strain energy release is a measurement of how much energy is present at each position on the leaflet to drive the growth of a defect in the lateral direction, i.e., between left and right sides as shown in FIGS. 3M-N.

As can be seen in FIGS. 3K-L, leaflet 110 experiences significantly reduced vertical strain energy release, which was calculated to be 110.331 joules per mm squared (J/mm2), as compared to 132.151 J/mm2 for leaflet 72. The most significantly reduced regions are shown in the lower center portion of leaflet 110 and in the upper corners of leaflet 110 where the free edge and base come together.

With respect to the lateral strain energy releases depicted in FIGS. 3M-N, leaflet 110 again experiences significant reductions as compared to leaflet 72. In this example, the lateral strain energy release for leaflet 110 was determined to be 61.315 J/mm2 and the lateral strain energy release for leaflet 72 was determined to be 71.097 J/mm2.

These significant reductions in strain energy release allows for the use of a wider range of materials in leaflets 110, such as those having lower cut-growth thresholds that may exhibit superior overall performance as compared to those having higher cut-growth thresholds. Alternatively, the same materials with high cut growth thresholds may be employed but with prospects for longer lifetime in use.

Figure 5A:
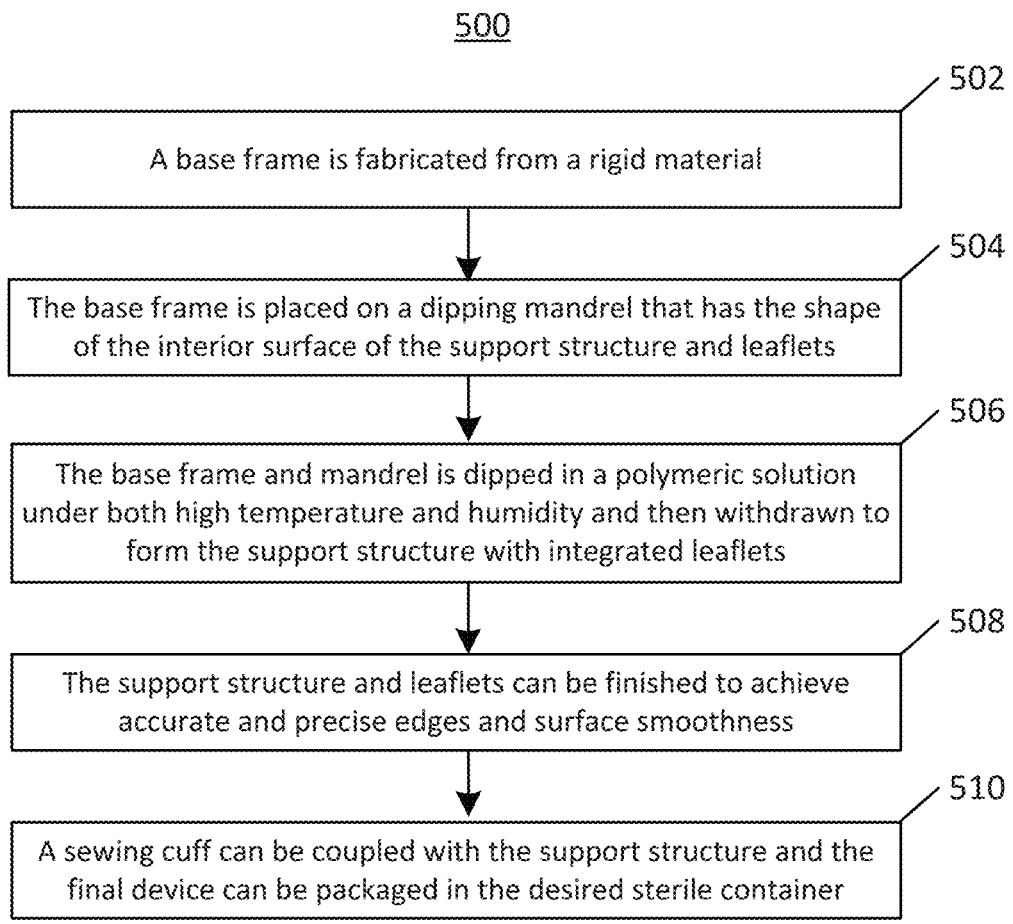
FIG. 5A is a flowchart depicting an example embodiment of a method of manufacturing a prosthetic heart valve.
Figure 5C:
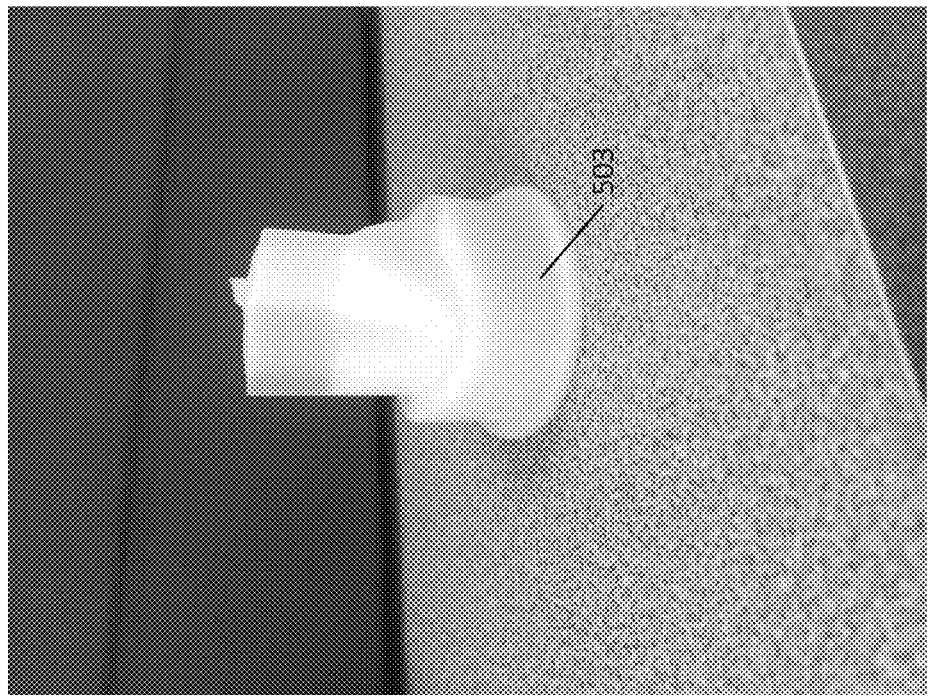
FIG. 5C is a photograph depicting an example embodiment of a base frame for use in a dip casting manufacturing method.
Figure 5B:
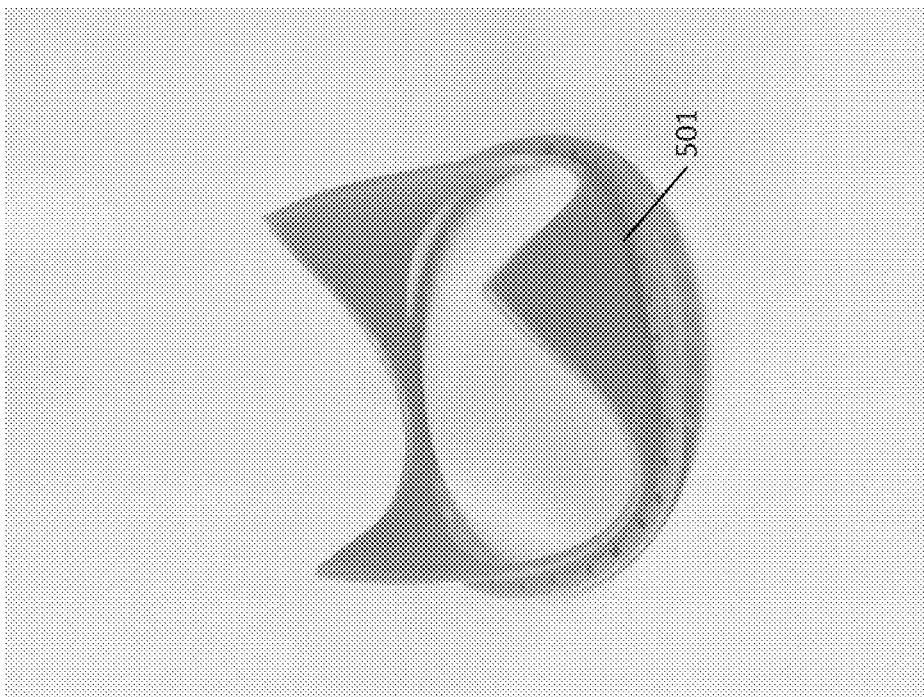
FIG. 5B is a photograph depicting an example embodiment of a mandrel for use in a dip casting manufacturing method.

Leaflets 110 are coupled to support structure 102 in a number of ways, such as adhesives, molding, casting, sewing, fasteners, and others known to those of ordinary skill in the art. FIG. 5A is a flow diagram depicting an example embodiment of a method 500 of manufacturing certain embodiments of prosthetic heart valve 100 using a dip casting process. At 502, a base frame is fabricated from a rigid material such as a polyether ether ketone (PEEK), a polyetherimide (PEI) such as ULTEM, and the like. This can be done by machining or injection molding. At 504, the base frame is placed on a dipping mandrel that has the shape of the interior surface of the support structure and leaflets. An example embodiment of a base frame 501 is depicted in the photograph of FIG. 5B. An example embodiment of a dipping mandrel 503, without the base frame, is depicted in the photograph of FIG. 5C. Mandrel 503 can be inserted into a polymeric solution with forming equipment that envelops the base frame and casts the leaflets in the desired form.

At 506, the base frame and mandrel is dipped in a polymeric solution under both high temperature and humidity and then withdrawn. Although the methods disclosed herein are not limited to such, in some example embodiments, the relative humidity (RH) can be in the range of 20-80% and the temperature can be in the range of 20-50 degrees C. Step 506 can result in a manifestation of support structure 102 and leaflets 111 together in an integrally formed but unfinished state.

Dipping step 506 can be performed only once to arrive at the fully formed (but unfinished) valve, or can be performed multiple times (e.g., two times, three times, or as many times as desired). In one embodiment, the base frame is fabricated from a first material (e.g., PEEK) different than the polymeric material from which the leaflets are fabricated. In that case it may be desirable to form the leaflets to the base frame only after the base frame has been pre-coated by the leaflet polymer to provide for greater cohesion. The base frame can be pre-coated by first dipping the base frame in the leaflet polymer having a first viscosity. This can be done with or without the mandrel. If done with the mandrel, the resulting leaflets can be removed. The pre-coated base frame can then be placed on the mandrel and dipped again, this time in the leaflet polymer with the same or a relatively higher viscosity. This second dipping can result in the formation of the full leaflet bodies integrally formed with the support structure. Use of a low viscosity followed by a higher viscosity can allow for formation of a thin pre-coating that does not significantly distort the shape of the underlying base frame followed by formation of the leaflets having the desired thickness.

At 508, support structure 102 and leaflets 111 can be trimmed and otherwise finished to achieve accurate and precise edges and surface smoothness. This can occur, for example, through laser cutting, ultrasonic trimming, water knife, a mechanical clam shell cutter, and the like. Finally, at 510, a sewing cuff can be coupled with support structure 102 and the final device can be packaged in the desired sterile container.

Those of ordinary skill in the art will readily recognize, in light of this description, the many variations of suitable dip casting procedures, pressures, and temperatures that are not stated here yet are suitable to fabricate the prosthetic heart valves described herein. Likewise, those of ordinary skill in the art will also recognize, in light of this description, the alternatives to dip casting that can be used to fabricate the prosthetic heart valves described herein.

As already mentioned, the embodiments of prosthetic heart valve 100 described herein can be directly implanted into the heart of the patient. In one such example procedure, the appropriate size replacement valve can be determined and then an open heart access procedure is performed by a surgeon to gain access to the malfunctioning valve of the heart that will be replaced. The surgeon can then position the selected prosthetic heart valve 100 in position over the malfunctioning valve and attach valve 100 to the surrounding tissue. The attachment can occur, for instance, by fastening the sewing cuff to the tissue with one or more sutures. Prior to attachment, if the surgeon determines that the selected valve size is not optimal, then a different valve having a different size can be selected and placed in position within the heart. In some other embodiments, the malfunctioning valve can be removed prior to positioning valve 100 in the intended location. Once valve 100 is attached, the open heart cavity is closed and the procedure is ended.

As used herein and in the appended claims, the singular forms "a", "an", and "the" include plural referents unless the context clearly dictates otherwise.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

What is claimed is:

1. A prosthetic heart valve, comprising:
 a support structure having a central axis oriented in the direction of blood flow through an interior of the support structure;
 only three artificial leaflets, each leaflet having a movable part with a base along the support structure and a free edge allowed to move independent of the support structure, the movable part of each leaflet also having a central axis extending between the base and the free edge, wherein the movable part of each leaflet is movable between a first position, for preventing the flow of blood through an interior of the support structure, and a second position, for allowing the flow of blood through the interior of the support structure, wherein the base of the movable part of each leaflet is the boundary where the movable part of the leaflet contacts the support structure, wherein the support structure is substantially cylindrical where the base of the movable part of each leaflet meets the support structure, and wherein a profile of the base of the movable part of the first leaflet is at least partially convex when viewed from an exterior side view of the support structure normal to a plane formed by the central axis of the support structure and the central axis of the movable part of the first leaflet when in the first position.

2. The prosthetic heart valve of claim 1, wherein the profile of the base of the movable part of the first leaflet is at least partially convex and at least partially concave when viewed from an exterior of the support structure along a normal to a plane formed by the central axis of the support structure and the central axis of the movable part of the first leaflet.

3. The prosthetic heart valve of claim 1, wherein, when a second one of the three leaflets is viewed from an exterior of the support structure along a normal to a plane formed by the central axis of the support structure and the central axis of the movable part of the second leaflet, a profile of the base of the movable part of the second leaflet is at least partially convex.

4. The prosthetic heart valve of claim 3, wherein, when a third one of the three leaflets is viewed from an exterior of the support structure along a normal to a plane formed by the central axis of the support structure and the central axis of the movable part of the third leaflet, a profile of the base of the movable part of the third leaflet is at least partially convex.

5. The prosthetic heart valve of claim 1, wherein the support structure comprises an annular base portion at an upstream end.

6. The prosthetic heart valve of claim 5, wherein the support structure comprises a sewing cuff at the annular base portion.

7. The prosthetic heart valve of claim 5, wherein the support structure comprises a plurality of extensions from the annular base portion, with the base of the movable part of each leaflet meeting two adjacent ones of the extensions.

8. The prosthetic heart valve of claim 1, wherein the artificial leaflets are polymeric.

9. The prosthetic heart valve of claim 1, wherein the prosthetic heart valve is not radially collapsible for placement into an intravascular delivery device.

10. The prosthetic heart valve of claim 1, wherein the prosthetic heart valve is not radially collapsible for placement in a trans-apical delivery device.

11. The prosthetic heart valve of claim 1, wherein the support structure and the plurality of leaflets are formed of the same material.

12. The prosthetic heart valve of claim 1, wherein the support structure and the plurality of leaflets are formed of different materials.

13. The prosthetic heart valve of claim 1, wherein each of the plurality of leaflets is a discrete body.

14. The prosthetic heart valve of claim 1, wherein the base of the movable part of each of the plurality of leaflets is sewn to the support structure.

15. The prosthetic heart valve of claim 1, wherein the base of the movable part of each of the three of leaflets is integrally formed to the support structure.

16. The prosthetic heart valve of claim 1, wherein the base of the movable part of each of the three of leaflets is a casting boundary between each leaflet and the support structure.

17. The prosthetic heart valve of claim 1, wherein the entirety of an inner lumen surface of the support structure is substantially cylindrical.

18. The prosthetic heart valve of claim 1, wherein the support structure is cylindrical where the base of the movable part of each leaflet transitions to the support structure.

* * * * *